US010773049B2

(12) United States Patent
Gaw et al.

(10) Patent No.: US 10,773,049 B2
(45) Date of Patent: Sep. 15, 2020

(54) COUGH-ASSIST SYSTEMS WITH HUMIDIFIER BYPASS

(71) Applicant: Ventec Life Systems, Inc., Bothell, WA (US)

(72) Inventors: Shan Gaw, Seattle, WA (US); Joseph Cipollone, Bothell, WA (US)

(73) Assignee: Ventec Life Systems, Inc., Bothell, WA (US)

( * ) Notice: Subject to any disclaimer, the term of this patent is extended or adjusted under 35 U.S.C. 154(b) by 948 days.

(21) Appl. No.: 15/188,722

(22) Filed: Jun. 21, 2016

(65) Prior Publication Data

US 2017/0361058 A1    Dec. 21, 2017

(51) Int. Cl.
*A61M 16/20*    (2006.01)
*A61M 16/00*    (2006.01)
(Continued)

(52) U.S. Cl.
CPC ...... *A61M 16/208* (2013.01); *A61M 16/0006* (2014.02); *A61M 16/0009* (2014.02);
(Continued)

(58) Field of Classification Search
CPC ............ A61M 16/208; A61M 16/0463; A61M 16/022; A61M 16/0006; A61M 16/0875;
(Continued)

(56) References Cited

U.S. PATENT DOCUMENTS 3,789,837 A    2/1974 Philips et al.
3,875,626 A    4/1975 Tysk et al.
(Continued)

FOREIGN PATENT DOCUMENTS

CN    103071215 A    5/2013
EP     0937478 B1    8/2003
(Continued)

OTHER PUBLICATIONS

US 8,012,240 B2, 09/2011, Sprinkle (withdrawn)
(Continued)

*Primary Examiner* — Tu A Vo
*Assistant Examiner* — Alexander Morales
(74) *Attorney, Agent, or Firm* — Perkins Coie LLP

(57) ABSTRACT

The present technology relates generally to cough-assist devices with humidified cough assistance. In one example, a system includes a cough-assist device having a first phase configured to provide insufflating gas to a patient circuit and a second phase configured to draw exsufflating gas from the patient circuit. A humidifier is disposed between the cough-assist device and a distal end of the patient circuit, the humidifier including a chamber configured to contain heated water and fluidically coupled to the cough-assist device and the patient circuit. The system further includes a bypass configured to (a) direct insufflating gas from the cough-assist device through a first route to the patient circuit such that the insufflating gas is humidified in the chamber, and (b) route exsufflating gas from the patient circuit through a second route to the cough-assist device such that the exsufflating gas bypasses the chamber.

19 Claims, 10 Drawing Sheets

(51) Int. Cl.
*A61M 16/16* (2006.01)
*A61M 16/10* (2006.01)
*A61M 16/08* (2006.01)
*A61M 16/04* (2006.01)
*A61M 16/14* (2006.01)

(52) U.S. Cl.
CPC ...... *A61M 16/0066* (2013.01); *A61M 16/022* (2017.08); *A61M 16/0463* (2013.01); *A61M 16/0875* (2013.01); *A61M 16/109* (2014.02); *A61M 16/16* (2013.01); *A61M 16/1055* (2013.01); *A61M 16/14* (2013.01); *A61M 2202/0208* (2013.01); *A61M 2205/502* (2013.01); *A61M 2205/8206* (2013.01)

(58) Field of Classification Search
CPC ............ A61M 16/0066; A61M 16/109; A61M 16/16; A61M 16/0009; A61M 16/1055; A61M 16/14; A61M 2205/502; A61M 2205/8206; A61M 2202/0208; A61M 16/10; A61M 16/1075–1085; A61M 16/1095; A61M 16/161–168
See application file for complete search history.

(56) References Cited

U.S. PATENT DOCUMENTS

| | | |
|---|---|---|
| 4,280,399 A | 7/1981 | Cunning |
| 4,331,455 A | 5/1982 | Sato |
| 4,357,936 A | 11/1982 | Ellestad et al. |
| 4,367,767 A | 1/1983 | Hurd |
| 4,386,945 A | 6/1983 | Gardner |
| 4,401,116 A | 8/1983 | Fry et al. |
| 4,417,573 A | 11/1983 | De Vries |
| 4,425,914 A | 1/1984 | Ray et al. |
| 4,449,990 A | 5/1984 | Tedford, Jr. |
| 4,450,838 A | 5/1984 | Miodownik |
| 4,459,982 A | 7/1984 | Fry |
| 4,502,873 A | 3/1985 | Mottram et al. |
| 4,516,424 A | 5/1985 | Rowland |
| 4,527,557 A | 7/1985 | Devries et al. |
| 4,545,790 A | 10/1985 | Miller et al. |
| 4,561,287 A | 12/1985 | Rowland |
| 4,576,616 A | 3/1986 | Mottram et al. |
| 4,602,653 A | 7/1986 | Ruiz-Vela et al. |
| 4,621,632 A | 11/1986 | Bartels et al. |
| 4,627,860 A | 12/1986 | Rowland |
| 4,637,386 A | 1/1987 | Baum |
| 4,648,395 A | 3/1987 | Sato et al. |
| 4,648,888 A | 3/1987 | Rowland |
| 4,681,099 A | 7/1987 | Sato et al. |
| 4,702,240 A | 10/1987 | Chaoui |
| 4,794,922 A | 1/1989 | Devries |
| 4,813,979 A | 3/1989 | Miller et al. |
| 4,869,733 A | 9/1989 | Stanford |
| 4,880,443 A | 11/1989 | Miller et al. |
| 4,905,685 A | 3/1990 | Olsson et al. |
| 4,936,297 A | 6/1990 | Greiff et al. |
| 4,971,609 A | 11/1990 | Pawlos |
| 4,983,190 A | 1/1991 | Verrando et al. |
| 4,993,269 A | 2/1991 | Guillaume et al. |
| 5,002,591 A | 3/1991 | Stanford |
| 5,014,694 A | 5/1991 | Devries |
| 5,021,137 A | 6/1991 | Joshi et al. |
| 5,034,023 A | 7/1991 | Thompson |
| 5,071,453 A | 12/1991 | Hradek et al. |
| 5,072,729 A | 12/1991 | Devries |
| 5,101,656 A | 4/1992 | Miller |
| 5,107,831 A | 4/1992 | Halpern et al. |
| 5,127,400 A | 7/1992 | Devries et al. |
| 5,129,924 A | 7/1992 | Schultz |
| 5,134,329 A | 7/1992 | Lang |
| 5,166,563 A | 11/1992 | Bassine |
| 5,169,506 A | 12/1992 | Michaels |
| 5,186,793 A | 2/1993 | Michaels |
| 5,265,594 A | 11/1993 | Olsson et al. |
| 5,273,031 A | 12/1993 | Olsson et al. |
| 5,275,642 A | 1/1994 | Bassine |
| 5,296,110 A | 3/1994 | Tabatabaie-Raissi |
| 5,331,995 A | 7/1994 | Westfall et al. |
| 5,335,426 A | 8/1994 | Settlemyer et al. |
| 5,354,361 A | 10/1994 | Coffield |
| 5,370,112 A | 12/1994 | Perkins |
| 5,378,345 A | 1/1995 | Taylor et al. |
| 5,397,443 A | 3/1995 | Michaels |
| 5,400,777 A | 3/1995 | Olsson et al. |
| 5,469,372 A | 11/1995 | McBrearty et al. |
| 5,474,062 A | 12/1995 | Devires et al. |
| 5,474,595 A | 12/1995 | McCombs |
| 5,494,028 A | 2/1996 | Devries et al. |
| 5,497,767 A | 3/1996 | Olsson et al. |
| 5,501,212 A | 3/1996 | Psaros |
| 5,540,220 A | 7/1996 | Gropper et al. |
| 5,540,233 A | 7/1996 | Larsson et al. |
| 5,575,283 A | 11/1996 | Sjoestrand |
| 5,578,115 A | 11/1996 | Cole |
| 5,694,924 A | 12/1997 | Cewers |
| 5,694,926 A | 12/1997 | Devries et al. |
| 5,701,883 A | 12/1997 | Hete et al. |
| 5,706,801 A | 1/1998 | Remes et al. |
| 5,720,277 A | 2/1998 | Olsson et al. |
| 5,740,796 A | 4/1998 | Skog |
| 5,743,253 A | 4/1998 | Castor et al. |
| 5,746,806 A | 5/1998 | Aylsworth et al. |
| 5,765,557 A | 6/1998 | Warters |
| 5,765,558 A | 6/1998 | Psaros et al. |
| 5,766,310 A | 6/1998 | Cramer |
| 5,810,324 A | 9/1998 | Eriksson et al. |
| 5,827,358 A | 10/1998 | Kulish et al. |
| 5,845,633 A | 12/1998 | Psaros |
| 5,849,219 A | 12/1998 | De et al. |
| 5,858,062 A | 1/1999 | McCulloh et al. |
| 5,858,063 A | 1/1999 | Cao et al. |
| 5,862,802 A | 1/1999 | Bird |
| 5,868,133 A | 2/1999 | Devries et al. |
| 5,871,564 A | 2/1999 | McCombs |
| 5,875,777 A | 3/1999 | Eriksson |
| 5,878,744 A | 3/1999 | Pfeiffer |
| 5,881,722 A | 3/1999 | Devries et al. |
| 5,893,944 A | 4/1999 | Dong |
| 5,896,857 A | 4/1999 | Hely et al. |
| 5,906,672 A | 5/1999 | Michaels et al. |
| 5,917,135 A | 6/1999 | Michaels et al. |
| 5,931,162 A | 8/1999 | Christian |
| 5,937,853 A | 8/1999 | Stroem |
| 5,948,142 A | 9/1999 | Holmes et al. |
| 5,957,130 A | 9/1999 | Krahbichler et al. |
| 5,968,236 A | 10/1999 | Bassine |
| 5,988,165 A | 11/1999 | Richey et al. |
| 5,997,617 A | 12/1999 | Czabala et al. |
| 6,010,555 A | 1/2000 | Smolarek et al. |
| 6,035,851 A | 3/2000 | Wallen |
| 6,062,218 A | 5/2000 | Krahbichler et al. |
| 6,068,680 A | 5/2000 | Kulish et al. |
| 6,073,630 A | 6/2000 | Adahan |
| 6,095,139 A | 8/2000 | Psaros |
| 6,102,038 A | 8/2000 | Devries |
| 6,112,744 A | 9/2000 | Hognelid |
| 6,113,673 A | 9/2000 | Loutfy et al. |
| 6,123,074 A | 9/2000 | Hete et al. |
| 6,152,132 A | 11/2000 | Psaros |
| 6,152,134 A | 11/2000 | Webber et al. |
| 6,152,135 A | 11/2000 | Devries et al. |
| 6,155,252 A | 12/2000 | Warters |
| 6,156,100 A | 12/2000 | Conrad et al. |
| 6,158,430 A | 12/2000 | Pfeiffer et al. |
| 6,162,283 A | 12/2000 | Conrad et al. |
| 6,176,897 B1 | 1/2001 | Keefer |
| 6,189,532 B1 | 2/2001 | Hely et al. |
| 6,190,441 B1 | 2/2001 | Czabala et al. |
| 6,192,885 B1 | 2/2001 | Jalde |
| 6,217,635 B1 | 4/2001 | Conrad et al. |
| 6,234,170 B1 | 5/2001 | Bergkvist |

(56) References Cited

U.S. PATENT DOCUMENTS

| | | |
|---|---|---|
| 6,253,767 B1 | 7/2001 | Mantz |
| 6,263,873 B1 | 7/2001 | Hedenberg |
| 6,269,811 B1 | 8/2001 | Duff |
| 6,298,848 B1 | 10/2001 | Skog |
| 6,302,107 B1 | 10/2001 | Richey et al. |
| 6,344,069 B2 | 2/2002 | Smolarek et al. |
| 6,346,139 B1 | 2/2002 | Czabala |
| 6,348,082 B1 | 2/2002 | Murdoch et al. |
| 6,360,740 B1 | 3/2002 | Ward et al. |
| 6,386,235 B1 | 5/2002 | McCulloh et al. |
| 6,393,802 B1 | 5/2002 | Bowser et al. |
| 6,394,089 B1 | 5/2002 | Cantrill et al. |
| 6,395,065 B1 | 5/2002 | Murdoch et al. |
| 6,412,483 B1 | 7/2002 | Jones et al. |
| 6,446,630 B1 | 9/2002 | Todd, Jr. |
| 6,471,744 B1 | 10/2002 | Hill |
| 6,478,850 B1 | 11/2002 | Warren |
| 6,478,857 B2 | 11/2002 | Czabala |
| 6,497,755 B2 | 12/2002 | Murdoch et al. |
| 6,514,318 B2 | 2/2003 | Keefer |
| 6,514,319 B2 | 2/2003 | Keefer et al. |
| 6,516,798 B1 | 2/2003 | Davies |
| 6,520,176 B1 | 2/2003 | Dubois et al. |
| 6,524,370 B2 | 2/2003 | Maheshwary et al. |
| 6,526,970 B2 | 3/2003 | Devries et al. |
| 6,532,956 B2 | 3/2003 | Hill |
| 6,547,851 B2 | 4/2003 | Warren |
| 6,551,384 B1 | 4/2003 | Ackley et al. |
| 6,553,992 B1 | 4/2003 | Berthon-Jones et al. |
| 6,558,451 B2 | 5/2003 | McCombs et al. |
| 6,564,798 B1 | 5/2003 | Jalde |
| 6,565,635 B2 | 5/2003 | Keefer et al. |
| 6,595,213 B2 | 7/2003 | Bennarsten |
| 6,601,583 B2 | 8/2003 | Pessala et al. |
| 6,622,726 B1 | 9/2003 | Du |
| 6,626,175 B2 | 9/2003 | Jafari et al. |
| 6,629,525 B2 | 10/2003 | Hill et al. |
| 6,640,807 B2 | 11/2003 | Bennarsten |
| 6,641,644 B2 | 11/2003 | Jagger et al. |
| 6,641,645 B1 | 11/2003 | Lee et al. |
| 6,644,312 B2 | 11/2003 | Berthon-Jones et al. |
| 6,651,652 B1 | 11/2003 | Waard |
| 6,651,658 B1 | 11/2003 | Hill et al. |
| 6,651,692 B2 | 11/2003 | Meckes et al. |
| 6,660,065 B2 | 12/2003 | Byrd et al. |
| 6,679,258 B1 | 1/2004 | Stroem |
| 6,691,702 B2 | 2/2004 | Appel et al. |
| 6,694,978 B1 | 2/2004 | Bennarsten |
| 6,702,880 B2 | 3/2004 | Roberts et al. |
| 6,712,876 B2 | 3/2004 | Cao et al. |
| 6,712,877 B2 | 3/2004 | Cao et al. |
| 6,739,334 B2 | 5/2004 | Valeij |
| 6,740,146 B2 | 5/2004 | Simonds |
| 6,755,193 B2 | 6/2004 | Berthon-Jones et al. |
| 6,756,216 B2 | 7/2004 | Berthon-Jones et al. |
| 6,761,166 B2 | 7/2004 | Ahlmen et al. |
| 6,764,534 B2 | 7/2004 | McCombs et al. |
| 6,782,888 B1 | 8/2004 | Friberg et al. |
| 6,793,719 B2 | 9/2004 | Kim et al. |
| 6,805,122 B2 | 10/2004 | Richey et al. |
| 6,811,590 B2 | 11/2004 | Lee et al. |
| 6,837,244 B2 | 1/2005 | Yagi et al. |
| 6,845,773 B2 | 1/2005 | Berthon-Jones et al. |
| 6,860,858 B2 | 3/2005 | Green et al. |
| 6,863,068 B2 | 3/2005 | Jamison et al. |
| 6,866,700 B2 | 3/2005 | Amann |
| 6,877,511 B2 | 4/2005 | Devries et al. |
| 6,889,726 B2 | 5/2005 | Richey et al. |
| 6,896,721 B1 | 5/2005 | Lynn |
| 6,908,503 B2 | 6/2005 | McCombs et al. |
| 6,910,480 B1 | 6/2005 | Berthon-Jones |
| 6,923,180 B2 | 8/2005 | Richey et al. |
| 6,935,460 B2 | 8/2005 | McCombs et al. |
| 6,949,133 B2 | 9/2005 | McCombs et al. |
| 6,997,881 B2 | 2/2006 | Green et al. |
| 7,000,610 B2 | 2/2006 | Bennarsten et al. |
| 7,032,592 B2 | 4/2006 | Castor et al. |
| 7,040,318 B2 | 5/2006 | Daescher et al. |
| 7,055,522 B2 | 6/2006 | Berthon-Jones |
| 7,066,985 B2 | 6/2006 | Deane et al. |
| 7,077,133 B2 | 7/2006 | Yagi et al. |
| 7,081,745 B2 | 7/2006 | Haveri |
| 7,089,937 B2 | 8/2006 | Berthon-Jones et al. |
| 7,094,275 B2 | 8/2006 | Keefer et al. |
| 7,100,609 B2 | 9/2006 | Berthon-Jones et al. |
| 7,105,038 B2 | 9/2006 | Lee et al. |
| 7,121,276 B2 | 10/2006 | Jagger et al. |
| 7,121,277 B2 | 10/2006 | Stroem |
| 7,135,059 B2 | 11/2006 | Deane et al. |
| 7,156,903 B2 | 1/2007 | McCombs |
| 7,171,963 B2 | 2/2007 | Jagger et al. |
| 7,179,326 B2 | 2/2007 | Nakamura et al. |
| 7,188,621 B2 | 3/2007 | Devries et al. |
| 7,213,468 B2 | 5/2007 | Fujimoto |
| 7,219,666 B2 | 5/2007 | Friberg et al. |
| 7,222,623 B2 | 5/2007 | Devries et al. |
| 7,250,073 B2 | 7/2007 | Keefer et al. |
| 7,255,103 B2 | 8/2007 | Bassin |
| 7,279,029 B2 | 10/2007 | Occhialini et al. |
| 7,294,170 B2 | 11/2007 | Richey et al. |
| 7,329,304 B2 | 2/2008 | Bliss et al. |
| 7,347,207 B2 | 3/2008 | Ahlmen et al. |
| 7,350,521 B2 | 4/2008 | Whitley et al. |
| 7,367,337 B2 | 5/2008 | Berthon-Jones et al. |
| 7,368,005 B2 | 5/2008 | Bliss et al. |
| RE40,402 E | 6/2008 | Bohm et al. |
| 7,402,193 B2 | 7/2008 | Bliss et al. |
| 7,427,315 B2 | 9/2008 | Dolensky et al. |
| 7,428,902 B2 | 9/2008 | Du et al. |
| 7,429,289 B2 | 9/2008 | Dolensky et al. |
| 7,431,032 B2 | 10/2008 | Jagger et al. |
| 7,438,745 B2 | 10/2008 | Deane et al. |
| 7,445,546 B2 | 11/2008 | Hondmann et al. |
| 7,445,663 B1 | 11/2008 | Hunter et al. |
| 7,455,717 B2 | 11/2008 | Sprinkle |
| 7,473,299 B2 | 1/2009 | Occhialini et al. |
| 7,491,261 B2 | 2/2009 | Warren et al. |
| 7,497,215 B1 | 3/2009 | Nguyen et al. |
| 7,510,601 B2 | 3/2009 | Whitley et al. |
| 7,517,385 B2 | 4/2009 | Winter |
| 7,524,365 B2 | 4/2009 | Lin |
| 7,527,053 B2 | 5/2009 | Devries et al. |
| 7,533,872 B2 | 5/2009 | Lee et al. |
| 7,550,031 B2 | 6/2009 | Hunter et al. |
| 7,550,036 B2 | 6/2009 | Lee et al. |
| 7,556,670 B2 | 7/2009 | Aylsworth et al. |
| 7,559,326 B2 | 7/2009 | Smith et al. |
| 7,585,351 B2 | 9/2009 | Deane et al. |
| 7,590,551 B2 | 9/2009 | Auer |
| 7,604,004 B2 | 10/2009 | Jagger et al. |
| 7,604,005 B2 | 10/2009 | Jagger et al. |
| 7,628,151 B2 | 12/2009 | Bassin |
| 7,637,989 B2 | 12/2009 | Bong |
| 7,655,059 B2 | 2/2010 | Wang et al. |
| 7,655,063 B2 | 2/2010 | Wang et al. |
| 7,682,428 B2 | 3/2010 | Nawata et al. |
| 7,682,429 B2 | 3/2010 | Dolensky et al. |
| 7,686,870 B1 | 3/2010 | Deane et al. |
| 7,704,304 B2 | 4/2010 | Warren et al. |
| 7,708,802 B1 | 5/2010 | Deane et al. |
| 7,708,818 B2 | 5/2010 | Clark |
| 7,717,981 B2 | 5/2010 | Labuda et al. |
| 7,722,700 B2 | 5/2010 | Sprinkle |
| 7,727,160 B2 | 6/2010 | Green et al. |
| 7,730,887 B2 | 6/2010 | Deane et al. |
| 7,753,996 B1 | 7/2010 | Deane et al. |
| 7,758,672 B2 | 7/2010 | Lee et al. |
| 7,763,103 B2 | 7/2010 | Dolensky et al. |
| 7,760,768 B2 | 8/2010 | Taylor et al. |
| 7,766,010 B2 | 8/2010 | Jagger et al. |
| 7,771,511 B2 | 8/2010 | Dolensky |
| 7,780,769 B2 | 8/2010 | Dolensky et al. |
| 7,794,522 B2 | 9/2010 | Bliss et al. |
| 7,828,878 B2 | 11/2010 | Zhong et al. |

(56) References Cited

U.S. PATENT DOCUMENTS

| | | | |
|---|---|---|---|
| 7,837,761 B2 | 11/2010 | Bliss et al. |
| 7,841,343 B2 | 11/2010 | Deane et al. |
| 7,849,854 B2 | 12/2010 | Devries et al. |
| 7,857,894 B2 | 12/2010 | Taylor et al. |
| 7,861,716 B2 | 1/2011 | Borrello |
| 7,866,315 B2 | 1/2011 | Jagger et al. |
| 7,874,290 B2 | 1/2011 | Chalvignac |
| 7,875,105 B2 | 1/2011 | Chambers et al. |
| 7,892,322 B2 | 2/2011 | Ono et al. |
| 7,909,034 B2 | 3/2011 | Sinderby et al. |
| 7,914,459 B2 | 3/2011 | Green et al. |
| 7,918,925 B2 | 4/2011 | Dolensky et al. |
| 7,922,789 B1 | 4/2011 | Deane et al. |
| 7,934,499 B2 | 5/2011 | Berthon-Jones |
| 7,954,493 B2 | 6/2011 | Nawata |
| 8,006,692 B2 | 8/2011 | Smith et al. |
| 8,016,916 B2 | 9/2011 | Ono et al. |
| 8,016,918 B2 | 9/2011 | Labuda et al. |
| 8,016,925 B2 | 9/2011 | McCombs et al. |
| 8,020,553 B2 | 9/2011 | Jagger et al. |
| 8,051,852 B2 | 11/2011 | Bassin |
| 8,062,003 B2 | 11/2011 | Goertzen et al. |
| 8,070,853 B2 | 12/2011 | Sprinkle |
| 8,070,864 B2 | 12/2011 | Uchiyama et al. |
| 8,070,922 B2 | 12/2011 | Nelson et al. |
| 8,075,676 B2 | 12/2011 | Thompson et al. |
| 8,100,125 B2 | 1/2012 | Duquette et al. |
| 8,118,024 B2 | 2/2012 | Devries et al. |
| 8,122,885 B2 | 2/2012 | Berthon-Jones et al. |
| 8,123,497 B2 | 2/2012 | Richey et al. |
| 8,142,544 B2 | 3/2012 | Taylor et al. |
| 8,146,596 B2 | 4/2012 | Smith et al. |
| 8,147,597 B2 | 4/2012 | Dolensky et al. |
| 8,156,937 B2 | 4/2012 | Devries et al. |
| 8,167,988 B2 | 5/2012 | Dolensky et al. |
| 8,192,526 B2 | 6/2012 | Zhong et al. |
| 8,210,205 B2 | 7/2012 | Michaels |
| 8,225,789 B2 | 7/2012 | Berthon-Jones |
| 8,226,745 B2 | 7/2012 | Siew-Wah et al. |
| 8,236,095 B1 | 8/2012 | Bassine |
| 8,256,419 B2 | 9/2012 | Sinderby et al. |
| 8,257,473 B2 | 9/2012 | Mccombs et al. |
| 8,280,498 B2 | 10/2012 | Jalde |
| 8,282,717 B2 | 10/2012 | Chambers et al. |
| 8,297,279 B2 | 10/2012 | Devries et al. |
| 8,337,599 B2 | 12/2012 | Kiritake |
| 8,343,259 B2 | 1/2013 | Knaebel |
| 8,349,053 B2 | 1/2013 | Lee et al. |
| 8,361,204 B1 | 1/2013 | Bassine |
| 8,366,815 B2 | 2/2013 | Taylor et al. |
| 8,371,298 B2 | 2/2013 | Hallbaeck et al. |
| 8,375,944 B2 | 2/2013 | Kwok |
| 8,377,180 B2 | 2/2013 | Maeda et al. |
| 8,377,181 B2 | 2/2013 | Taylor et al. |
| 8,386,548 B2 | 3/2013 | Green et al. |
| 8,388,745 B1 | 3/2013 | Pelletier et al. |
| 8,400,290 B2 | 3/2013 | Baker, Jr. |
| 8,418,691 B2 | 4/2013 | Jafari et al. |
| 8,418,692 B2 | 4/2013 | Sanchez |
| 8,424,520 B2 | 4/2013 | Thiessen |
| 8,424,521 B2 | 4/2013 | Jafari et al. |
| 8,428,672 B2 | 4/2013 | Sherman et al. |
| 8,434,480 B2 | 5/2013 | Jafari et al. |
| 8,434,482 B2 | 5/2013 | Borrello |
| 8,434,488 B2 | 5/2013 | Li et al. |
| 8,435,013 B2 | 5/2013 | Kondou et al. |
| 8,440,004 B2 | 5/2013 | Taylor et al. |
| 8,443,294 B2 | 5/2013 | Skidmore et al. |
| 8,448,640 B2 | 5/2013 | Bassin |
| 8,448,641 B2 | 5/2013 | Jafari et al. |
| 8,469,026 B2 | 6/2013 | Blomberg et al. |
| 8,522,780 B2 | 9/2013 | Devries et al. |
| 8,539,952 B2 * | 9/2013 | Carbone ............... A61M 16/20 128/205.24 |
| 8,627,819 B2 | 1/2014 | Devries et al. |
| 8,683,997 B2 | 4/2014 | Devries et al. |
| 8,770,191 B2 | 7/2014 | Tham |
| 8,844,530 B2 | 9/2014 | Birnkrant |
| 9,126,002 B2 | 9/2015 | Devries et al. |
| 9,345,851 B2 * | 5/2016 | Kim ............... A61M 16/208 |
| 9,504,799 B2 * | 11/2016 | Hardin ............. A61M 16/0816 |
| 9,956,371 B2 | 5/2018 | DeVries |
| 10,046,134 B2 | 8/2018 | DeVries |
| 10,105,509 B2 | 10/2018 | DeVries |
| 10,245,406 B2 | 4/2019 | DeVries |
| 10,350,377 B2 * | 7/2019 | Fiorenza ........... A61M 16/0875 |
| 2002/0005197 A1 | 1/2002 | DeVries |
| 2002/0053286 A1 | 5/2002 | Czabala |
| 2002/0092420 A1 | 7/2002 | Jagger et al. |
| 2002/0121278 A1 | 9/2002 | Hete |
| 2003/0000531 A1 | 1/2003 | Tuck |
| 2003/0010208 A1 | 1/2003 | Jagger et al. |
| 2003/0024766 A1 | 2/2003 | Briscoe |
| 2003/0051729 A1 | 3/2003 | Be et al. |
| 2003/0111077 A1 | 6/2003 | Van Hooser |
| 2003/0131848 A1 | 7/2003 | Stenzler |
| 2003/0196550 A1 | 10/2003 | Keefer et al. |
| 2003/0200865 A1 | 10/2003 | McCombs et al. |
| 2003/0230308 A1 | 12/2003 | Linden |
| 2004/0021108 A1 | 2/2004 | Hallback et al. |
| 2004/0231913 A1 | 11/2004 | McCombs et al. |
| 2005/0045040 A1 | 3/2005 | McCombs |
| 2005/0072298 A1 | 4/2005 | Deane et al. |
| 2005/0072306 A1 | 4/2005 | Deane et al. |
| 2005/0072423 A1 | 4/2005 | Deane et al. |
| 2005/0072426 A1 | 4/2005 | Deane et al. |
| 2005/0103341 A1 | 5/2005 | Deane et al. |
| 2005/0112013 A1 | 5/2005 | Devries et al. |
| 2005/0217481 A1 | 10/2005 | Dunne et al. |
| 2005/0257686 A1 | 11/2005 | Occhialini et al. |
| 2005/0274815 A1 | 12/2005 | Bergholtz et al. |
| 2006/0011065 A1 | 1/2006 | Hastings |
| 2006/0064802 A1 | 3/2006 | Damrath et al. |
| 2006/0086251 A1 | 4/2006 | Sprinkle |
| 2006/0102181 A1 | 5/2006 | McCombs et al. |
| 2006/0107947 A1 * | 5/2006 | Rist .................... A61M 11/00 128/200.14 |
| 2006/0117957 A1 | 6/2006 | McCombs et al. |
| 2006/0137522 A1 | 6/2006 | Nishimura et al. |
| 2006/0174871 A1 | 8/2006 | Jagger et al. |
| 2006/0174875 A1 | 8/2006 | Jagger et al. |
| 2006/0174877 A1 | 8/2006 | Jagger et al. |
| 2006/0230924 A1 | 10/2006 | Deane et al. |
| 2006/0230929 A1 | 10/2006 | Bliss et al. |
| 2006/0230931 A1 | 10/2006 | Bliss et al. |
| 2006/0230939 A1 | 10/2006 | Bliss et al. |
| 2006/0266357 A1 | 11/2006 | McCombs et al. |
| 2006/0283325 A1 | 12/2006 | Sugano |
| 2007/0031302 A1 | 2/2007 | Wittrup et al. |
| 2007/0056583 A1 | 3/2007 | Jagger et al. |
| 2007/0056584 A1 | 3/2007 | Jagger et al. |
| 2007/0084342 A1 | 4/2007 | Hunter et al. |
| 2007/0084349 A1 | 4/2007 | Calkins et al. |
| 2007/0101999 A1 | 5/2007 | Duquette et al. |
| 2007/0135757 A1 | 6/2007 | Acker |
| 2007/0144521 A1 | 6/2007 | Devries et al. |
| 2007/0148016 A1 | 6/2007 | Crawford et al. |
| 2007/0199566 A1 | 6/2007 | Be Eri Eliezer |
| 2007/0169623 A1 | 7/2007 | Lee et al. |
| 2007/0214955 A1 | 9/2007 | Aylsworth et al. |
| 2007/0227360 A1 | 10/2007 | Atlas et al. |
| 2007/0227540 A1 | 10/2007 | Ljungberg et al. |
| 2007/0272243 A1 | 11/2007 | Sherman et al. |
| 2007/0289446 A1 | 12/2007 | Occhialini et al. |
| 2008/0028933 A1 | 2/2008 | Ross et al. |
| 2008/0034975 A1 | 2/2008 | Chambers et al. |
| 2008/0053441 A1 | 3/2008 | Gottlib |
| 2008/0066616 A1 | 3/2008 | Sprinkle |
| 2008/0087170 A1 | 4/2008 | Deane et al. |
| 2008/0092892 A1 | 4/2008 | Boyle et al. |
| 2008/0092893 A1 | 4/2008 | Boyle et al. |
| 2008/0110338 A1 | 5/2008 | Taylor et al. |
| 2008/0110461 A1 | 5/2008 | Mulqueeny et al. |
| 2008/0135044 A1 | 6/2008 | Freitag et al. |

(56) References Cited

U.S. PATENT DOCUMENTS

| | | |
|---|---|---|
| 2008/0185544 A1 | 8/2008 | Yeh |
| 2008/0196580 A1 | 8/2008 | Bliss et al. |
| 2008/0202337 A1 | 8/2008 | Taylor et al. |
| 2008/0202508 A1 | 8/2008 | McClain et al. |
| 2008/0251071 A1 | 10/2008 | Armitstead et al. |
| 2008/0257145 A1 | 10/2008 | Sprinkle et al. |
| 2008/0257349 A1 | 10/2008 | Hedner et al. |
| 2008/0282880 A1 | 11/2008 | Bliss et al. |
| 2008/0302362 A1* | 12/2008 | Kwok .................. A61M 16/16 128/203.16 |
| 2008/0302363 A1 | 12/2008 | Kroupa |
| 2008/0314385 A1 | 12/2008 | Brunner et al. |
| 2008/0315441 A1 | 12/2008 | Lee et al. |
| 2009/0007912 A1 | 1/2009 | Lindell et al. |
| 2009/0025560 A1 | 1/2009 | Takemasa |
| 2009/0025564 A1 | 1/2009 | Kuwabara |
| 2009/0044698 A1 | 2/2009 | Meacham |
| 2009/0065007 A1 | 3/2009 | Wilkinson et al. |
| 2009/0065526 A1 | 3/2009 | Sprinkle |
| 2009/0071333 A1 | 3/2009 | Labuda et al. |
| 2009/0078251 A1 | 3/2009 | Zucchi et al. |
| 2009/0084381 A1 | 4/2009 | Devries et al. |
| 2009/0107500 A1 | 4/2009 | Edwards |
| 2009/0133368 A1 | 5/2009 | Calkins et al. |
| 2009/0133694 A1 | 5/2009 | Solci et al. |
| 2009/0145428 A1 | 6/2009 | Sward et al. |
| 2009/0167698 A1 | 7/2009 | Altas et al. |
| 2009/0188502 A1 | 7/2009 | Tiedje |
| 2009/0211448 A1 | 8/2009 | McClain |
| 2009/0229459 A1 | 9/2009 | Warren et al. |
| 2009/0250059 A1 | 10/2009 | Allum et al. |
| 2009/0301477 A1* | 12/2009 | Pierro ............... A61M 16/1045 128/201.13 |
| 2009/0308396 A1 | 12/2009 | McClain |
| 2010/0024819 A1 | 2/2010 | Tiedje |
| 2010/0051030 A1 | 3/2010 | Richard et al. |
| 2010/0052293 A1 | 3/2010 | Brooks et al. |
| 2010/0078018 A1 | 4/2010 | Heinonen |
| 2010/0095841 A1 | 4/2010 | Naheiri |
| 2010/0116270 A1 | 5/2010 | Edwards et al. |
| 2010/0122699 A1 | 5/2010 | Birnkrant |
| 2010/0126249 A1 | 5/2010 | Matsuzaki |
| 2010/0229867 A1 | 9/2010 | Bertinetti et al. |
| 2010/0275921 A1 | 11/2010 | Schindhelm et al. |
| 2010/0282084 A1 | 11/2010 | Taylor et al. |
| 2010/0288279 A1 | 11/2010 | Seiver et al. |
| 2010/0294127 A1 | 11/2010 | Dolensky |
| 2011/0000489 A1 | 1/2011 | Laksov et al. |
| 2011/0030684 A1 | 2/2011 | Wilkinson et al. |
| 2011/0030685 A1 | 2/2011 | Wilkinson et al. |
| 2011/0030686 A1 | 2/2011 | Wilkinson et al. |
| 2011/0030687 A1 | 2/2011 | Wilkinson et al. |
| 2011/0030689 A1 | 2/2011 | Wilkinson et al. |
| 2011/0057651 A1 | 3/2011 | Duric et al. |
| 2011/0067699 A1 | 3/2011 | Caruso et al. |
| 2011/0073115 A1 | 3/2011 | Wood et al. |
| 2011/0113964 A1 | 5/2011 | Chambers et al. |
| 2011/0154986 A1 | 6/2011 | Lee et al. |
| 2011/0197882 A1 | 6/2011 | Truschel et al. |
| 2011/0192122 A1 | 8/2011 | Whitesel et al. |
| 2011/0197883 A1 | 8/2011 | McDaniel et al. |
| 2011/0197884 A1 | 8/2011 | Duff et al. |
| 2011/0197887 A1 | 8/2011 | Truschel et al. |
| 2011/0209706 A1 | 9/2011 | Truschel et al. |
| 2011/0209707 A1 | 9/2011 | Terhark |
| 2011/0220107 A1 | 9/2011 | Kimm et al. |
| 2011/0232483 A1 | 9/2011 | Haberland et al. |
| 2011/0232645 A1 | 9/2011 | Smith |
| 2011/0247616 A1 | 10/2011 | Von et al. |
| 2011/0247620 A1 | 10/2011 | Armstrong et al. |
| 2011/0247621 A1 | 10/2011 | Richard et al. |
| 2011/0247622 A1 | 10/2011 | Schneider et al. |
| 2011/0259334 A1 | 10/2011 | Alfieri et al. |
| 2011/0297153 A1 | 12/2011 | Grimsey |
| 2011/0303223 A1 | 12/2011 | Kane et al. |
| 2011/0315140 A1 | 12/2011 | Shuman |
| 2012/0000462 A1 | 1/2012 | Edwards et al. |
| 2012/0006199 A1 | 1/2012 | McCombs et al. |
| 2012/0006326 A1 | 1/2012 | Ahmad |
| 2012/0012109 A1 | 1/2012 | Chalvignac |
| 2012/0017909 A1 | 1/2012 | Porges et al. |
| 2012/0027628 A1 | 2/2012 | Ogawa |
| 2012/0037159 A1 | 2/2012 | Mulqueeny et al. |
| 2012/0055340 A1 | 3/2012 | Wilkinson et al. |
| 2012/0055474 A1 | 3/2012 | Wilkinson |
| 2012/0055475 A1 | 3/2012 | Wilkinson |
| 2012/0055477 A1 | 3/2012 | Wilkinson |
| 2012/0055480 A1 | 3/2012 | Wilkinson |
| 2012/0055482 A1 | 3/2012 | Wilkinson |
| 2012/0055483 A1 | 3/2012 | Wilkinson et al. |
| 2012/0060640 A1 | 3/2012 | Refsland et al. |
| 2012/0125336 A1 | 5/2012 | Berthon-Jones et al. |
| 2012/0125337 A1 | 5/2012 | Asanoi |
| 2012/0152248 A1 | 6/2012 | Richey, et al. |
| 2012/0167883 A1 | 7/2012 | Taylor et al. |
| 2012/0167886 A1 | 7/2012 | Taylor et al. |
| 2012/0167887 A1 | 7/2012 | Taylor et al. |
| 2012/0167888 A1 | 7/2012 | Taylor et al. |
| 2012/0177546 A1 | 7/2012 | Hilbig |
| 2012/0192667 A1 | 8/2012 | Lewis et al. |
| 2012/0192862 A1 | 8/2012 | Lewis et al. |
| 2012/0192864 A1 | 8/2012 | Galbraith et al. |
| 2012/0247329 A1 | 10/2012 | Hilbig |
| 2012/0266883 A1 | 10/2012 | Taylor et al. |
| 2012/0285543 A1 | 11/2012 | Michaels |
| 2012/0291884 A1 | 11/2012 | Yamaura et al. |
| 2012/0304867 A1 | 12/2012 | Watanabe et al. |
| 2012/0308779 A1 | 12/2012 | Klee et al. |
| 2012/0318145 A1 | 12/2012 | Hilbig et al. |
| 2013/0008438 A1 | 1/2013 | Sugawara et al. |
| 2013/0008444 A1 | 1/2013 | Chalvignac et al. |
| 2013/0025591 A1 | 1/2013 | Clark et al. |
| 2013/0031784 A1 | 2/2013 | Chambers et al. |
| 2013/0087145 A1 | 4/2013 | Koebrich et al. |
| 2013/0087146 A1 | 4/2013 | Callaghan et al. |
| 2013/0092159 A1 | 4/2013 | Ulrichskoetter et al. |
| 2013/0098361 A1 | 4/2013 | Koebrich et al. |
| 2013/0104898 A1 | 5/2013 | Berthon-Jones |
| 2013/0125891 A1 | 5/2013 | Eddy |
| 2013/0186400 A1 | 7/2013 | Jafari et al. |
| 2013/0186401 A1 | 7/2013 | Jafari et al. |
| 2013/0199520 A1* | 8/2013 | Dhuper ............ A61M 16/0816 128/200.23 |
| 2013/0255689 A1 | 10/2013 | Kim et al. |
| 2013/0272905 A1 | 10/2013 | Shelke |
| 2013/0276789 A1* | 10/2013 | Garde ............... A61M 16/0066 128/204.23 |
| 2014/0007878 A1 | 1/2014 | Armistead et al. |
| 2014/0116441 A1 | 5/2014 | McDaniel |
| 2014/0216446 A1 | 8/2014 | Wruck |
| 2014/0318535 A1 | 10/2014 | Bullock |
| 2015/0000660 A1 | 1/2015 | Martin |
| 2015/0224278 A1 | 8/2015 | Addington et al. |
| 2015/0283352 A1* | 10/2015 | Karkkainen .......... A61M 16/16 128/203.26 |
| 2015/0320962 A1 | 11/2015 | Bafile |
| 2016/0243330 A1 | 8/2016 | Destefano |
| 2016/0279363 A1 | 9/2016 | Devries et al. |
| 2016/0279369 A1 | 9/2016 | Cipollone |
| 2016/0279378 A1 | 9/2016 | Cipollone |
| 2017/0000968 A1* | 1/2017 | Harrington ......... A61M 16/026 |
| 2017/0361058 A1 | 12/2017 | Gaw et al. |
| 2019/0054268 A1 | 2/2019 | Devries et al. |

FOREIGN PATENT DOCUMENTS

| | | |
|---|---|---|
| WO | 9908738 A1 | 2/1999 |
| WO | 03045486 A1 | 6/2003 |
| WO | 2013/033589 A1 | 3/2013 |
| WO | 2014176454 A1 | 10/2014 |

(56) References Cited

FOREIGN PATENT DOCUMENTS

| WO | 2015126853 A1 | 8/2015 |
|----|---------------|--------|
| WO | 2016067147 A1 | 5/2016 |

OTHER PUBLICATIONS

Rodriquez et al., "Maximizing Oxygen Delivery During Mechanical Ventilation with a Portable Oxygen Concentrator," Journal of Trauma—Injury Infection & Critical Care, 69(1), Jul. 2010, pp. S87-S93.
Gustafson et al., "Pulse Dose Delivery of Oxygen in Mechanically Ventilated Pigs with Acute Lung Injury," The Journal of Trauma and Acute Care Surgery, 75(5), Nov. 2013, pp. 775-779.
Branson, D. Richard et al., "Maximizing Oxygen Delivery During Mechanical Ventilation With a Portable Oxygen Concentrator," The Journal of TRAUMA® Injury, Infection, and Critical Care, vol. 69, No. 1, July Supplement 2010, 7 pages.
International Search Report & Written Opinion received for counterpart International Application No. PCT/US2017/037738; dated Sep. 6, 2017; (8 pages).
Extended European Search Report dated Sep. 24, 2018 in European Patent Application No. 16769634.3, 7 pages.
International Search Report and Written Opinion dated Jun. 10, 2016 in International Patent Application No. PCT/US2016/023828, 11 pages.
Extended European Search Report dated Dec. 16, 2019 in European Patent Application No. 17815960.4, 6 pages.

\* cited by examiner

COUGH-ASSIST SYSTEMS WITH HUMIDIFIER BYPASS

TECHNICAL FIELD

The present technology is generally related to humidifiers for ventilation and cough-assist systems.

BACKGROUND

Mechanical ventilators are used to assist with breathing. Conventional ventilators typically drive inspiratory gases including oxygen into the patient's lungs. Many patients who use a ventilator also need other types of assistance related to treating and maintaining their airways and lungs, such as cough assistance. Currently, to receive cough assistance, a patient must be disconnected from the mechanical ventilator and connected to a separate cough-assist device. After cough assistance is performed, the patient must be disconnected from the cough-assist device and reconnected to the mechanical ventilator. Often, the patient airway is also suctioned after the patient has been disconnected from the cough-assist device and reconnected to the mechanical ventilator to remove remaining secretions in the patient airway after the cough assistance. Because this process may be tedious, it is often not performed in a manner that is most advantageous to the patient.

Thus, a need exists for ventilators to provide additional functionality beyond delivering inspiratory gases into the patient's lungs, such as cough assistance and humidification. The present technology provides these and other advantages as will be apparent from the following detailed description and accompanying figures.

DETAILED DESCRIPTION

Figure 1:
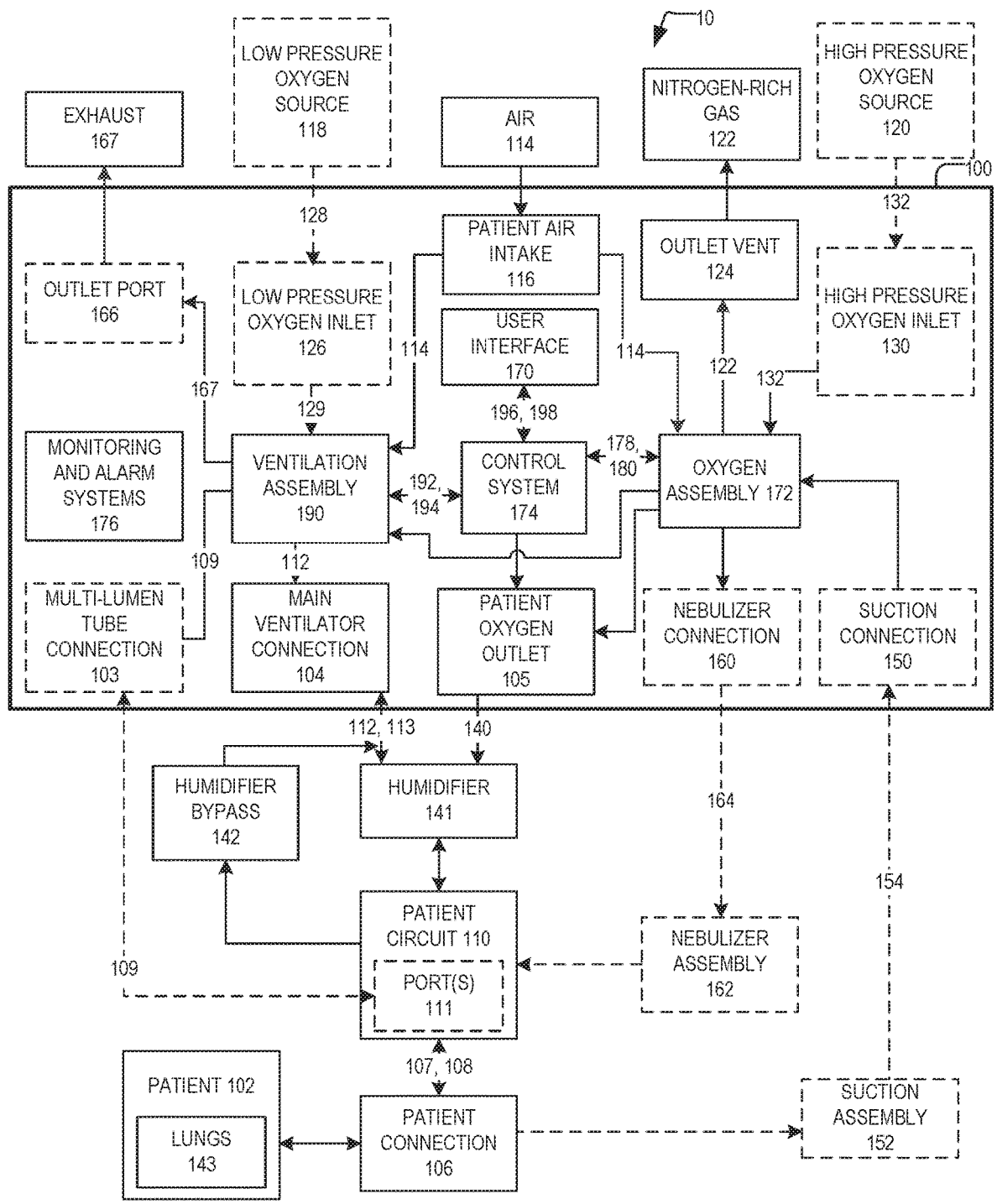
FIG. 1 is a block diagram illustrating a system that includes a ventilator for use by a human patient.

Patients on ventilators often need humidification of both the inspiratory gas provided to the patient and insufflation gas for assisted cough therapy (also referred to as mechanical insufflation-exsufflation). Equipping a ventilator with cough-assistance capabilities eliminates the need to change the patient circuit to transition between ventilation and cough therapy. However, the present inventors have noted that the high exsufflation flows during cough assistance that pass through the humidifier chamber cause water to travel back to the ventilator. To alleviate this problem, the present technology is directed to a humidifier bypass that permits insufflating gas to pass through a humidifier chamber to the patient and routes exsufflating gas back to the ventilator without passing through the humidifier chamber.

The purpose of the ventilator bypass is to redirect the exsufflation flow around the humidifier chamber to prevent the exsufflation flow from blowing water in the chamber back to the ventilator. The bypass can be a passive accessory that connects to standard commercially available humidifier chambers. The bypass can remain in line between the ventilator and the patient following cough therapy. When ventilation resumes, the inspired gas is delivered through the humidifier chamber as if the bypass were not present.

In addition, the bypass may also be used by ventilator patients with standalone cough-assist machines. Typically, the patient circuit is disconnected at the patient to perform cough therapy. Dedicated patient tubing on the cough machine is then connected to the patient. With invasive ventilation, patients can experience discomfort when manipulating tubing so close to the tracheostomy site and there is some risk of accidental decannulation. And, in this scenario, humidified gas is no longer delivered to the patient until ventilation resumes and the humidifier is back in line. Humidifier bypass systems in accordance with embodiments of the present technology enable the patient circuit to be disconnected anywhere between the ventilator and humidifier rather than disconnecting at the patient. Humidified gas is accordingly delivered during insufflation, but the bypass prevents ingress of water from the humidifier into the cough-assist machine during exsufflation.

Further specific details of several embodiments of the present technology are described below with reference to FIGS. 1-5B. Although many of the embodiments are described below with respect to devices, systems, and methods for ventilation with humidified cough assistance, other embodiments are within the scope of the present technology. Additionally, other embodiments of the present technology can have different configurations, components, and/or procedures than those described herein. For example, other embodiments can include additional elements and features beyond those described herein, or other embodiments may not include several of the elements and features shown and described herein.

For ease of reference, throughout this disclosure identical reference numbers are used to identify similar or analogous components or features, but components identified by the same reference number are not necessarily identical. Indeed, in many examples described herein, the identically numbered parts are distinct in structure and/or function.

FIG. 1 is a block diagram illustrating a system 10 that includes a ventilator 100 with integrated humidified cough assistance in accordance with the embodiment of the present technology. Several general aspects of the system 10 will be described initially to provide an understanding of the components related to embodiments of the humidified bypass devices of the present technology. The ventilator 100 may be configured to provide both traditional volume-controlled ventilation and pressure-controlled ventilation. The ventilator 100 has an optional multi-lumen tube connection 103, a main ventilator connection 104, and a patient oxygen outlet 105. The system 100 also has a patient connection 106 (e.g., a tracheal tube, a nasal mask, a mouthpiece, and the like) and a patient circuit 110 that fluidically couples the patient connection 106 to the main ventilator connection 104 and/or the patient oxygen outlet 105.

The patient circuit 110 may be an active patient circuit or a passive patient circuit. Optionally, when the patient circuit 110 is an active patient circuit, the patient circuit 110 may include one or more ports 111 configured to be connected to the optional multi-lumen tube connection 103. The port(s) 111 allow one or more pressure signals 109 to flow between the optional multi-lumen tube connection 103 and the patient circuit 110. The pressure signals 109 may be gas(es) obtained from a fluid (and/or gas) source for which a pressure is to be measured. The gas(es) obtained are at the same pressure as the fluid (and/or gas) source.

The system 100 further includes humidifier 141 in line with the patient circuit 110 and the main ventilator connection 104. In some embodiments, the patient circuit 110 includes a tube or conduit that extends between the humidifier 141 and the main ventilator connection 104 in addition to a tube or conduit that extends between the humidifier 141 and the patient connection 106. The system 100, or more specifically the humidifier 141, can be equipped with a bypass 142 as described in more detail below.

The main ventilator connection 104 is configured to provide gases 112 that include air 114 optionally mixed with oxygen. While identified as being "air," those of ordinary skill in the art appreciate that the air 114 may include ambient air or pressurized air obtained from any source external to the ventilator 100. The gases 112 may be inspiratory gases for the inspiratory phase of a breath or insufflation gases for the insufflation phase of cough assistance. The main ventilator connection 104 is configured to receive gases 113, which may include exsufflation gases exhaled by the patient 102 during an exsufflation phase of cough assistance.

The air 114 is received by the ventilator 100 via a patient air intake 116. Oxygen that is optionally mixed with the air 114 may be generated internally by the ventilator 100 and/or received from an optional low pressure oxygen source 118 (e.g., an oxygen concentrator), and/or an optional high pressure oxygen source 120. When the oxygen is generated internally, the ventilator 100 may output exhaust gases (e.g., nitrogen-rich gas 122) via an outlet vent 124. Optionally, the ventilator 100 may include a low pressure oxygen inlet 126 configured to be coupled to the optional low pressure oxygen source 118 and receive optional low pressure oxygen 128 therefrom. The ventilator 100 may include an optional high pressure oxygen inlet 130 configured to be coupled to the optional high pressure oxygen source 120 and receive optional high pressure oxygen 132 therefrom.

The patient oxygen outlet 105 is configured to provide doses or pulses of oxygen 140 to the patient connection 106 via the patient circuit 110 that are synchronized with the patient's breathing. Unlike the gases 112 provided by the main ventilator connection 104, the pulses of oxygen 140 do not include the air 114.

The gases 112 and/or the pulses of oxygen 140 delivered to the humidifier 141 and the patient circuit 110 are conducted thereby as inspiratory or insufflation gases 108 to the patient connection 106, which at least in part conducts those gases into the patient's lung(s) 143. Whenever the patient exhales during the exhalation phase of a breath or exsufflates during an exsufflation phase of cough assistance, exhaled gases 107 enter the patient circuit 110 via the patient connection 106. Thus, the patient circuit 110 may contain one or more of the following gases: the gases 112 provided by the ventilator 100, the pulses of oxygen 140, and the exhaled gases 107. For ease of illustration, the gases inside the patient circuit 110 will be referred to hereafter as "patient gases."

The ventilator 100 can optionally include a suction connection 150 configured to be coupled to an optional suction assembly 152. The ventilator 100 may provide suction 154 to the optional suction assembly 152 via the optional suction connection 150. The suction assembly 152 may be configured to be connected to the patient connection 106, a suction catheter (not shown) positionable inside the patient connection 106, and/or a drain (not shown).

The ventilator 100 can additionally include an optional nebulizer connection 160 configured to be coupled to an optional nebulizer assembly 162. The ventilator 100 may provide gases 164 (e.g., the air 114) to the optional nebulizer assembly 162 via the optional nebulizer connection 160. The optional nebulizer assembly 162 may be configured to be connected to the patient circuit 110. However, this is not a requirement. Optionally, the ventilator 100 may include an outlet port 166 through which exhaust 167 may exit from the ventilator 100.

The ventilator 100 may be configured to be portable and powered by an internal battery (not shown) and/or an external power source (not shown) such as a conventional wall outlet. The ventilator 100 further includes a ventilation assembly 190, a user interface 170, an oxygen assembly 172, a control system 174, and conventional monitoring and alarm systems 176. The control system 174 receives input information 196 (e.g., settings, parameter values, and the like) from the user interface 170, and provides output information 198 (e.g., performance information, status information, and the like) to the user interface 170. The user interface 170 is configured to receive input from a user (e.g., a caregiver, a clinician, and the like associated with a patient 102) and provide that input to the control system 174 in the input information 196. The user interface 170 is also configured to display the output information 198 to the user.

The ventilation assembly 190 may receive one or more control signals 192 from the control system 174, and the ventilation assembly 190 may provide one or more data signals 194 to the control system 174. The ventilation assembly 190 may also receive the pressure signals 109 from the patient circuit 110 via the multi-lumen connection 103. The oxygen assembly 172 may receive one or more control signals 178 from the control system 174, and the oxygen assembly 172 may provide one or more data signals 180 to the control system 174. The control signals 192 and 178 and the data signals 194 and 180 may be used by the control system 174 to monitor and/or control internal operations of the ventilator 100.

Figure 2A:
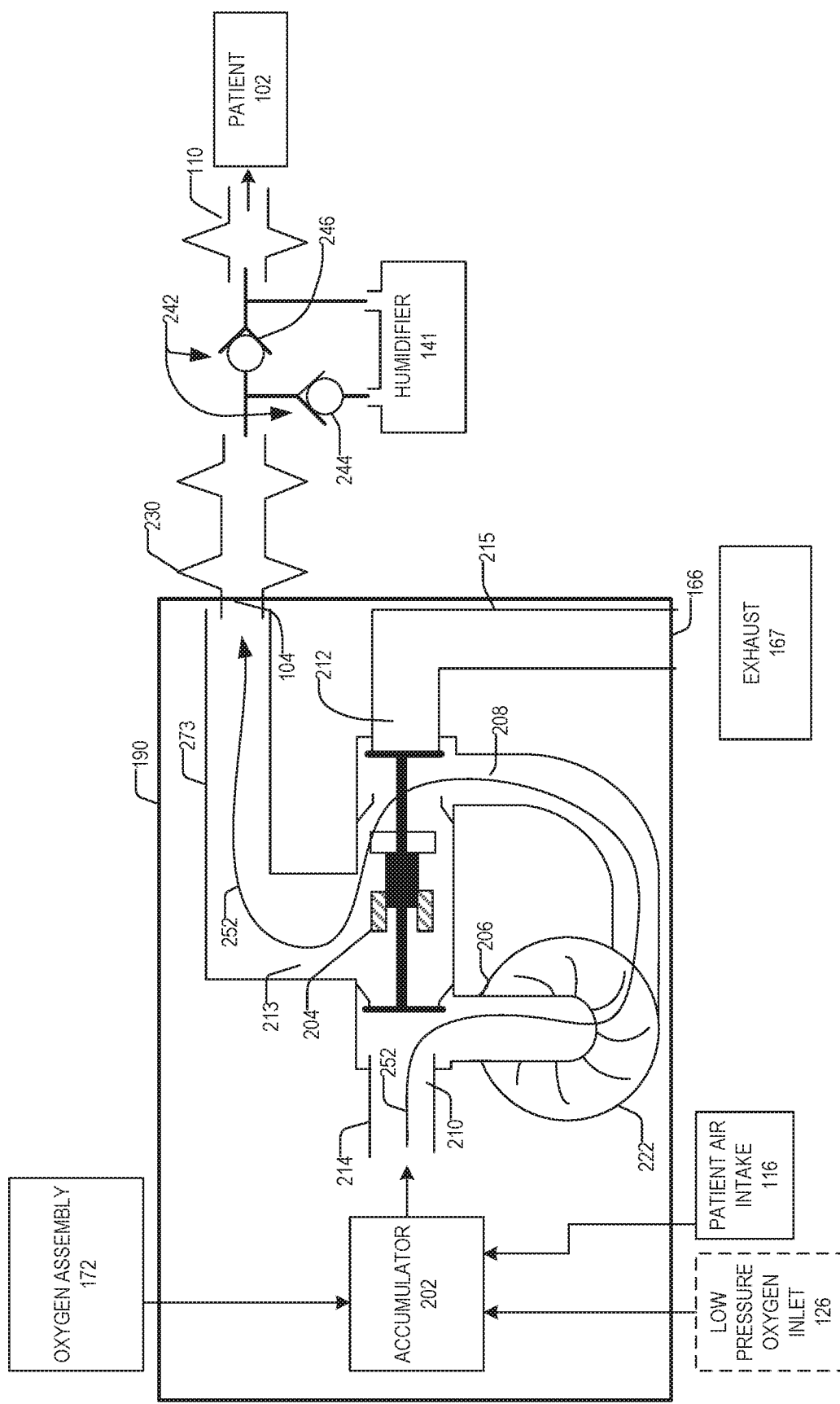
FIG. 2A is a schematic diagram illustrating components of a ventilator assembly of the ventilator of FIG. 1 with a cough-assist valve of the ventilator assembly depicted in a first configuration.
Figure 2B:
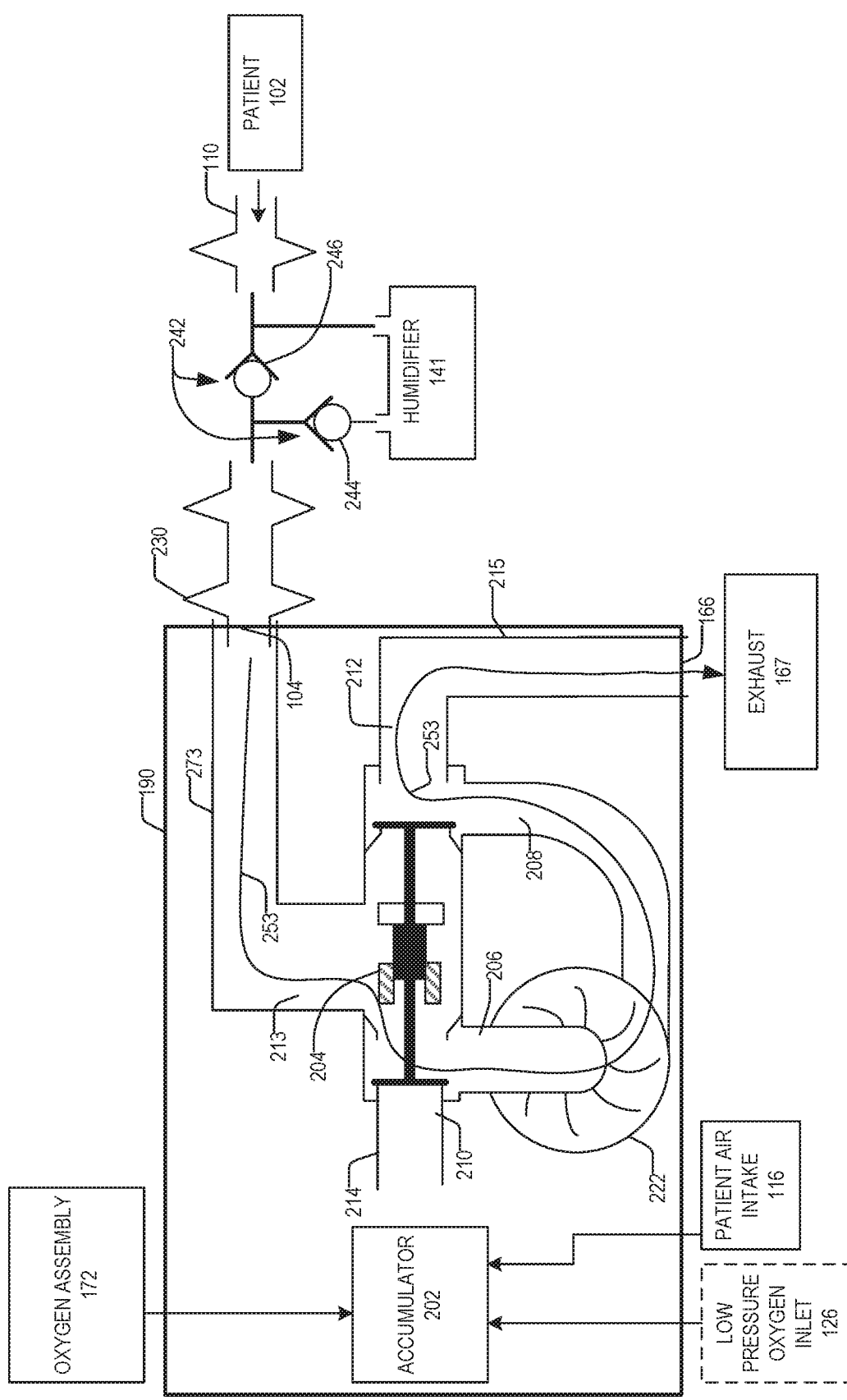
FIG. 2B is a schematic diagram illustrating the cough-assist valve of the ventilator assembly in a second configuration.

FIGS. 2A and 2B are schematic diagrams illustrating an embodiment of the ventilation assembly 190, the humidifier 141, and a bypass system 242. Referring to FIGS. 2A and 2B, the ventilation assembly 190 includes a cough-assist valve 204, an accumulator 202 and an internal bacteria filter 230. The cough-assist valve 204 is connected to (a) the accumulator 202 by a conduit or flow line 214, (b) the outlet port 166 by a conduit or flow line 215, and (c) the main ventilator connection 104 by a conduit or flow line 273. FIG. 2A depicts the cough-assist valve 204 in a first configuration for normal breathing and the insufflation phase of cough assistance, and FIG. 2B depicts the cough-assist valve 204 in a second configuration for the exsufflation phase of cough assistance.

Referring to FIG. 2A, in the first configuration, the cough-assist valve 204 receives a gas 252 from the accumulator 202 (via the flow line 214), and outputs the gas 252 to the main ventilator connection 104 (via the flow line 273). The gas 252 flowing through both the blower 222 and the cough-assist valve 204 during the inspiratory phase of a breath or the insufflation phase of a cough-assist maneuver performed by the ventilator 100 (see FIG. 1). During normal breathing/ventilation and the insufflation phase of cough assistance, the cough-assist valve 204 remains in the first configuration. Typical pressure ranges used to support normal breathing and ventilation can be from about 10-40 cm $H_2O$ during inspiration and from about 0-10 cm $H_2O$ during expiration. During cough assistance, the cough-assist valve 204 is in the first configuration (FIG. 2A) during the insufflation phase and the second configuration (FIG. 2B) during the exsufflation phase. Typical pressure ranges used provide cough-assist functionality are generally higher than for normal breathing/ventilation, such as from about 30-70 cm $H_2O$ during insufflation and from about negative 30-70 cm $H_2O$ during exsufflation.

The cough-assist valve 204 has a valve-to-blower outlet 206, a blower-to-valve inlet 208, an air intake 210, an exhaust outlet 212, and an aperture 213. The aperture 213 is connected to the main ventilator connection 104 by the flow line 273. As shown in FIG. 2A, when the cough-assist valve 204 is in the first configuration, the air intake 210 is in fluid communication with the valve-to-blower outlet 206, and the blower-to-valve inlet 208 is in fluid communication with the aperture 213. Further, the exhaust outlet 212 is closed such that both the valve-to-blower outlet 206 and the air intake 210 are in fluid communication with the aperture 213 via only the blower 222. Thus, the gas 252 may flow into the air intake 210, through a portion of the cough-assist valve 204 to the valve-to-blower outlet 206, and into the blower 222. The gas 252 exiting the blower 222 flows into the blower-to-valve inlet 208, through another portion of the cough-assist valve 204, and into the aperture 213. The aperture 213 is connected to the flow line 273, which conducts the gas 252 to the main ventilator connection 104.

During inspiration or insufflation, the gas 252 passes through the main ventilator connection 104, across the bacterial filter 230 and to the bypass system 242. In the embodiment shown in FIG. 2A, the bypass system 242 has a first valve 244 coupled to the humidifier 141 and a second valve 246. During normal breathing/ventilation and insufflation, the gas 252 flows through a first valve 244 and into the humidifier 141 where it is humidified. The gas 252 then is passed through the output of the bypass system 242 and to the patient circuit 110. The second valve 246 of the bypass system 242 prevents the gas 252 from passing directly to the patient circuit 110 without first going through the humidifier 141. The operation of the bypass system 242 is described in more detail below with respect to FIGS. 3-5B.

Referring to FIG. 2B, in the second configuration, the cough-assist valve 204 receives exsufflation gases 253 via the flow line 273 and outputs the exsufflation gases 253 (as the exhaust 167) to the outlet port 166 via the flow line 215. The exsufflation gases 253 flow through both the blower 222 and the cough-assist valve 204 during an exsufflation phase of cough assistance performed by the ventilator 100 (see FIG. 1).

As shown in FIG. 2B, when the cough-assist valve 204 is in the second configuration, the air intake 210 is closed, and the blower-to-valve inlet 208 and the exhaust outlet 212 are in fluid communication with the aperture 213 only via the blower 222. Further, the aperture 213 is in fluid communication with the valve-to-blower outlet 206, and the blower-to-valve inlet 208 is in fluid communication with the exhaust outlet 212. Thus, the exsufflation gases 253 flow into the aperture 213, across a portion of the cough-assist valve 204, to the valve-to-blower outlet 206, and into the blower 222. The exsufflation gas 253 exiting the blower 222 flows into the blower-to-valve inlet 208, through a portion of the cough-assist valve 204, and exits the cough-assist valve 204 though the exhaust outlet 212. The exhaust outlet 212 is connected to the flow line 215, which conducts the exsufflation gas 253 to the outlet port 166.

During exsufflation, the gas 253 passes through the patient circuit 110, through the second valve 246 of the bypass system 242, and across the bacterial filter 230 before reaching the main ventilator connection 104. The second valve 246 of the bypass system 242 permits the gas 253 to pass to the main ventilator connection 104, while the first valve 244 of the bypass system 242 prevents the gas 253 from passing back through the humidifier 141. For example, the first valve 244 closes during exsufflation flow to prohibit the gas 253 from passing back through the humidifier 141 to the main ventilator connection 144. As a result, the high velocity exsufflation gas 253 cannot entrain liquid from the humidifier 141 into the flow of gas 253 back into the ventilator 100. The operation of the bypass system 242 is described in more detail below with respect to FIGS. 3-5B.

Figure 3:
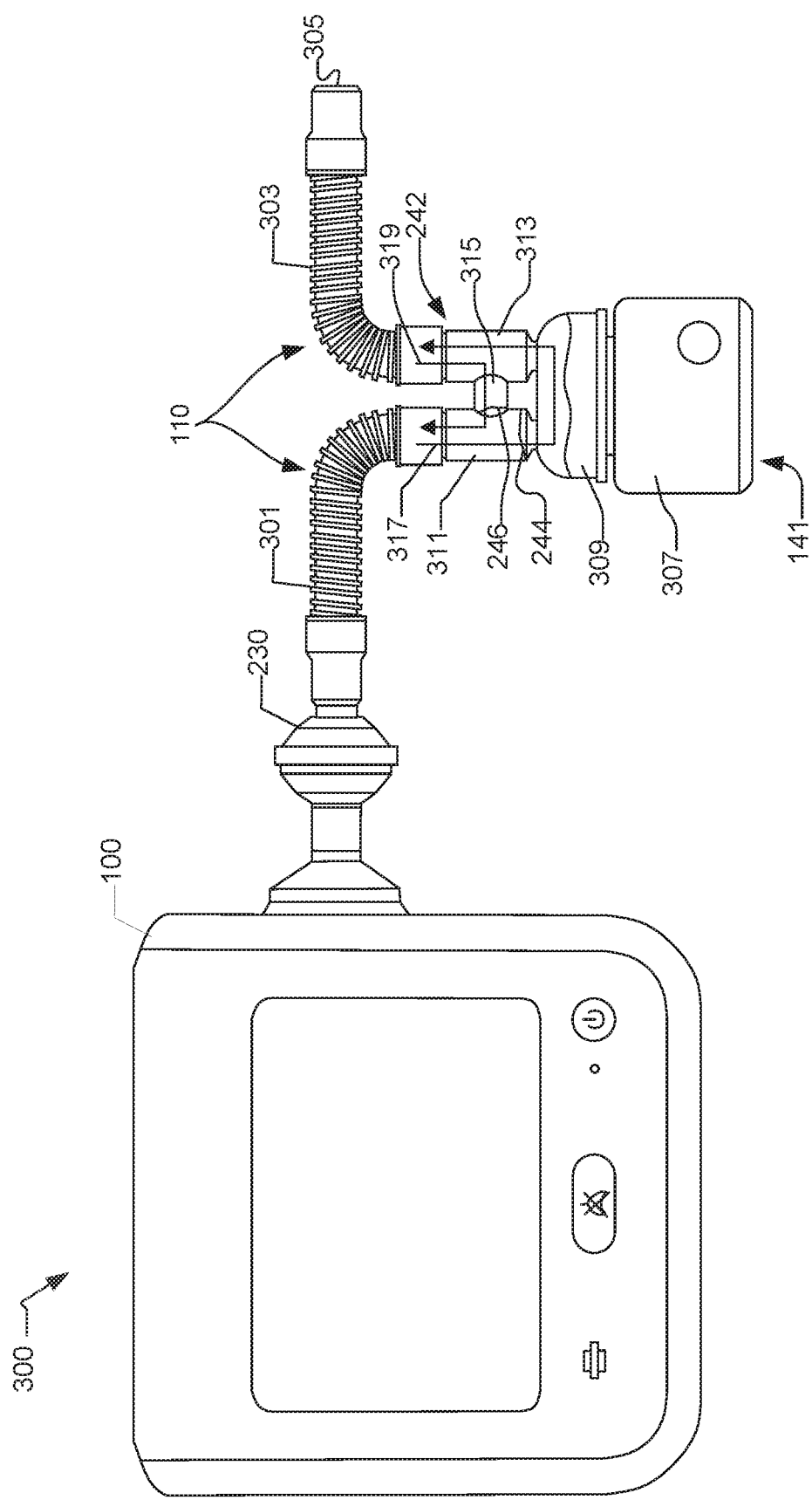
FIG. 3 illustrates a ventilation system including a ventilator with integrated cough-assist functionality, a patient circuit, a humidifier, and a humidifier bypass system.

FIG. 3 illustrates a system 300 including the ventilator 100 with integrated cough-assist functionality that is coupled to a patient circuit 110 and a humidifier 141 equipped with an embodiment of the bypass system 242. As illustrated, this embodiment of the humidifier 141 and the bypass system 242 are in line with the patient circuit 110. The patient circuit 110 includes a first tube 301 connected to the bacterial filter 230 and one side of the bypass system 242, and a second tube 303 connected to another side of the bypass system 242. A distal end 305 of the second tube 303 can be connected to the patient connection 106 (FIG. 1).

The humidifier 141 includes a base 307 having an integrated heater and a chamber 309 configured to retain water. In operation, the base 307 heats the water in the chamber 309 to produce water vapor. As a result, inspiration and insufflation gases passing through the chamber 309 are humidified before being delivered to the patient.

The bypass system 242 is in fluid communication with the chamber 309 as well as the first tube 301 and the second tube 303 of the patient circuit 110. In particular, the bypass system 242 includes a first conduit 311 that extends between the chamber 309 of the humidifier 141 and the first tube 301 of the patient circuit 110. The bypass system 242 additionally includes a second conduit 313 that extends between the chamber 309 of the humidifier 141 and the second tube 303 of the patient circuit 110. The bypass system 242 can also include a bridge 315 that is fluidically coupled to and extends between the first conduit 311 and the second conduit 313 at a position spaced apart from the chamber 309.

The first valve 244 is disposed in the first conduit 311 in a position below the intersection of the bridge 315 and the first conduit 311. The first valve 244 can be a one-way valve configured to open when the pressure is higher in the first tube 301 than the chamber 309, but close when the pressure in the chamber 309 is higher than in the first tube 301. As such, during inspiration or insufflation, gas flows from the ventilator 100, from the first tube 301 of the patient circuit 110 through the first conduit 311 and through the first valve 244 into the chamber 309 of the humidifier 141. However, during exhalation or exsufflation, gas is prevented from flowing back through the chamber 309 and up the first conduit 311.

The second valve 246 is disposed in the bridge 315 of the bypass system 242. The second valve 246 can be a one-way valve configured to open towards the first conduit 311 such that, during exsufflation, gas from the patient flows from the second tube 303 of the patient circuit 110 through the second conduit 313, through the bridge 315, and through second valve 246 towards the ventilator 100. Thus, the opposite one-way directions and the positions of the first and second valves 244 and 246 direct the high-velocity exsufflation gas flow to the ventilator 100 without passing through the humidifier 141.

The first and second valves 244, 246 can be many different types of valves. For example, one or both of the valves 244, 246 can be ball check valves, diaphragm check valves, leaf valves, swing check valves, tilting disc check valves, clapper valves, or any other suitable valve that allows flow in one direction while disallowing flow in the opposite direction. The first and second valves 244, 246 can be passive valves configured to open in the presence of flow in one direction without the need for actuation. In other embodiments, one or both of the valves can be active valves that are electronically controlled to open or close in response to signals communicated from a controller (see FIG. 5).

The system 300 provides a first flowpath 317 through the bypass system 242. The first flowpath 317 receives gas flowing from the ventilator 100 through the first tube 301 of the patient circuit 110 and into the first conduit of the bypass system 242. The first valve 244 opens in the presence of gas flowing in the direction of the first flowpath 317 while the second valve 246 is closed. The first flowpath 317 therefore continues through the first valve 244, through the chamber 309 of the humidifier 141, and into the second conduit 313 of the bypass system 242. The first flowpath 317 delivers gas into the second tube 303 of the patient circuit 110 where it then passes through the distal end 305 of the patient circuit 110 and to the patient. In this first flowpath 317, the gases (e.g., gases provided by the ventilator 100 either in breathing assistance (inspiration) or cough-assistance (insufflation) mode) are humidified before reaching the distal end 305 of the patient circuit 110 and being delivered to the patient.

The system 300 also provides a second flowpath 319 through the bypass system 242. The second flowpath 319 receives gas flowing from the distal end 305 of the patient circuit 110 through the second tube 303 of the patient circuit and into the second conduit 313 of the bypass system 242. The first valve 244 remains closed in the presence of gas flowing in the direction of the second flowpath 319 while the second valve 246 is open. As a result, the second flowpath 319 continues through the bridge 315 and out through the first conduit 311 of the bypass system 242. The second flowpath 319 delivers gas into the first tube 301 of the patient circuit 110 where it then passes through the bacterial filter 230 and into the ventilator 100. In this second flowpath 319, the gases (e.g., exsufflation gases drawn from the patient during cough assistance) do not pass through the chamber 309 of the humidifier 141. As a result, the risk of liquid from the chamber 309 being passed through the first tube 301 of the patient circuit 110 into the bacterial filter 230 and/or the ventilator 100 is reduced.

Figure 4A:
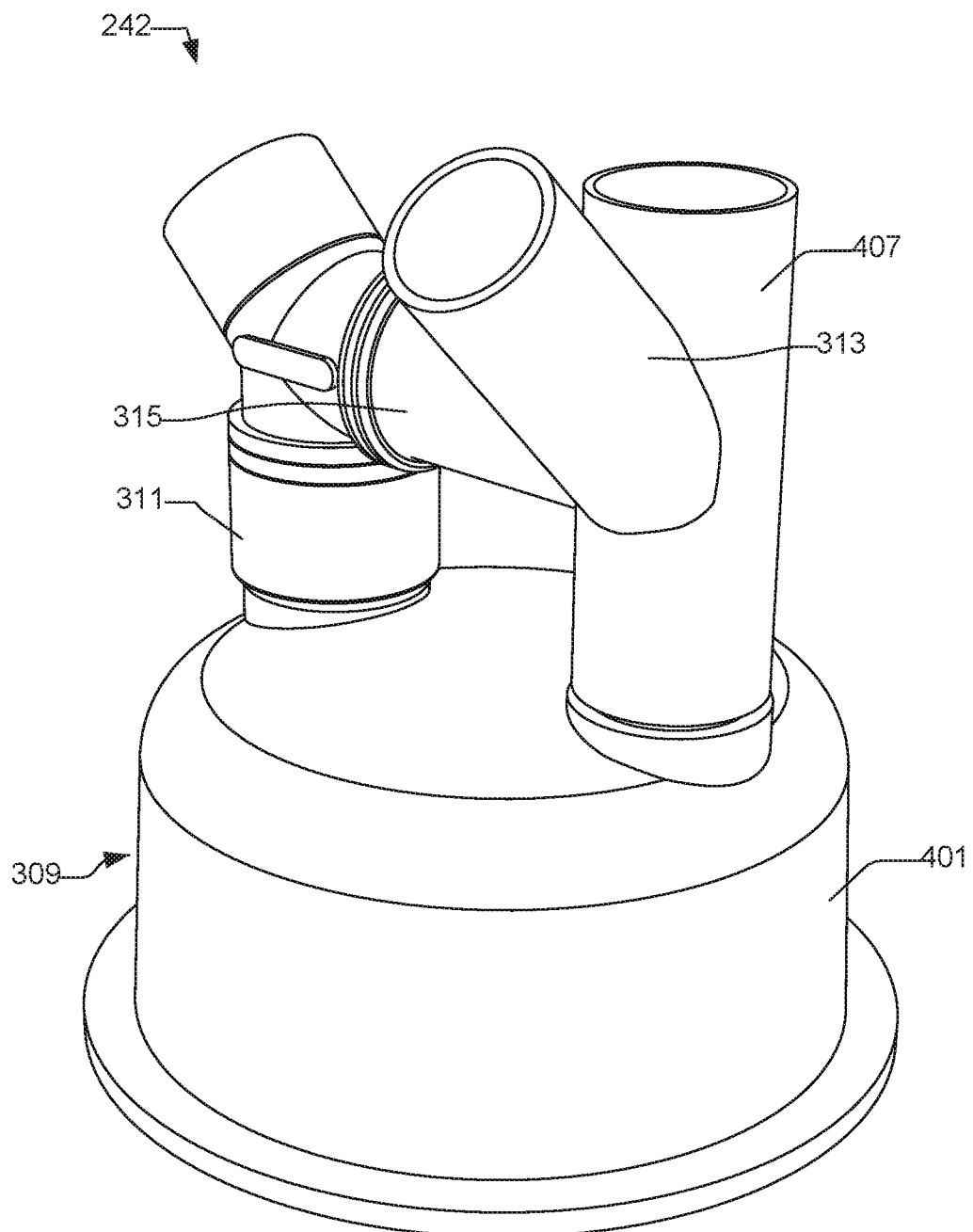
FIGS. 4A-4D illustrate various views of a humidifier bypass system.
Figure 4B:
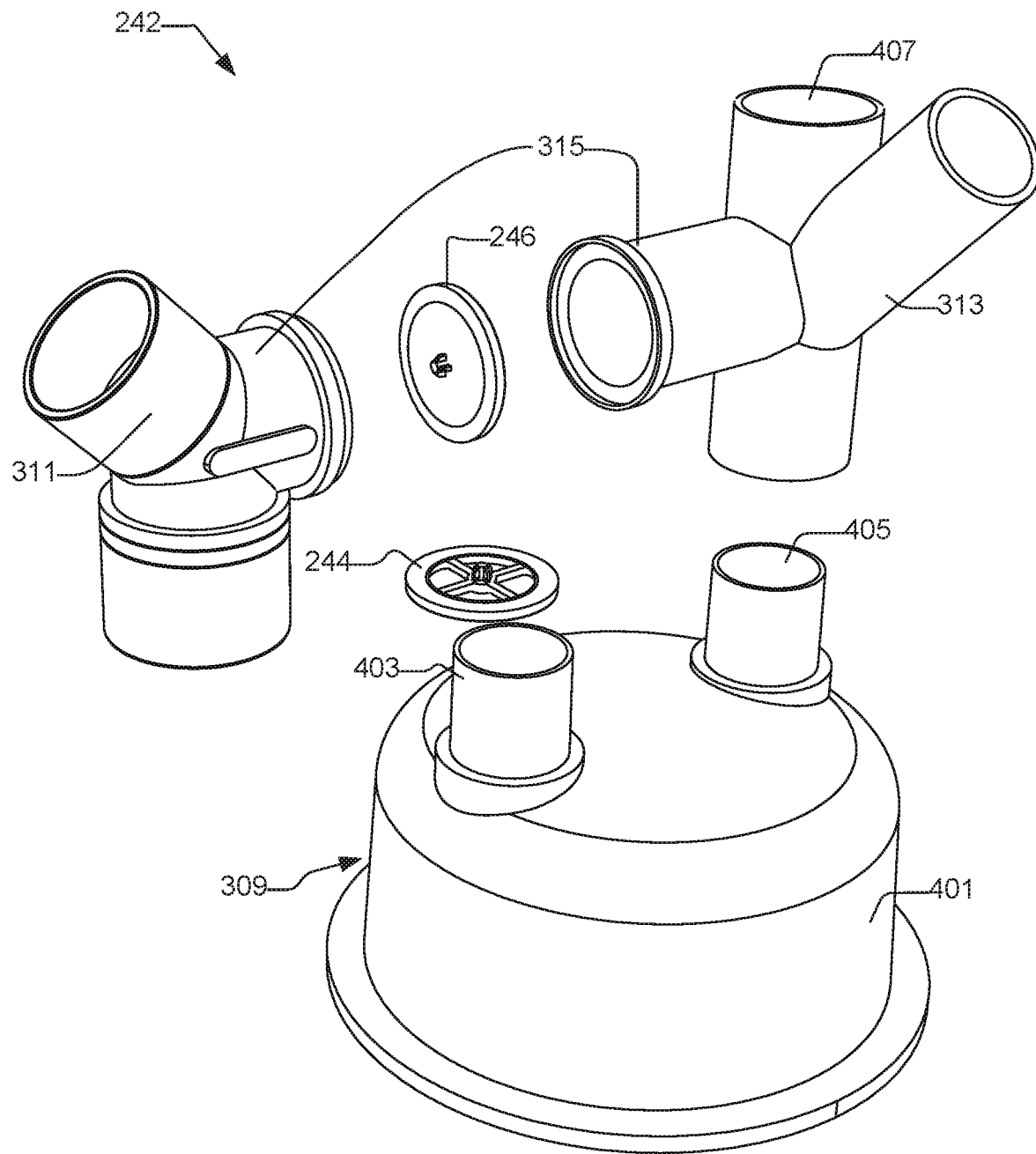
Figure 4C:
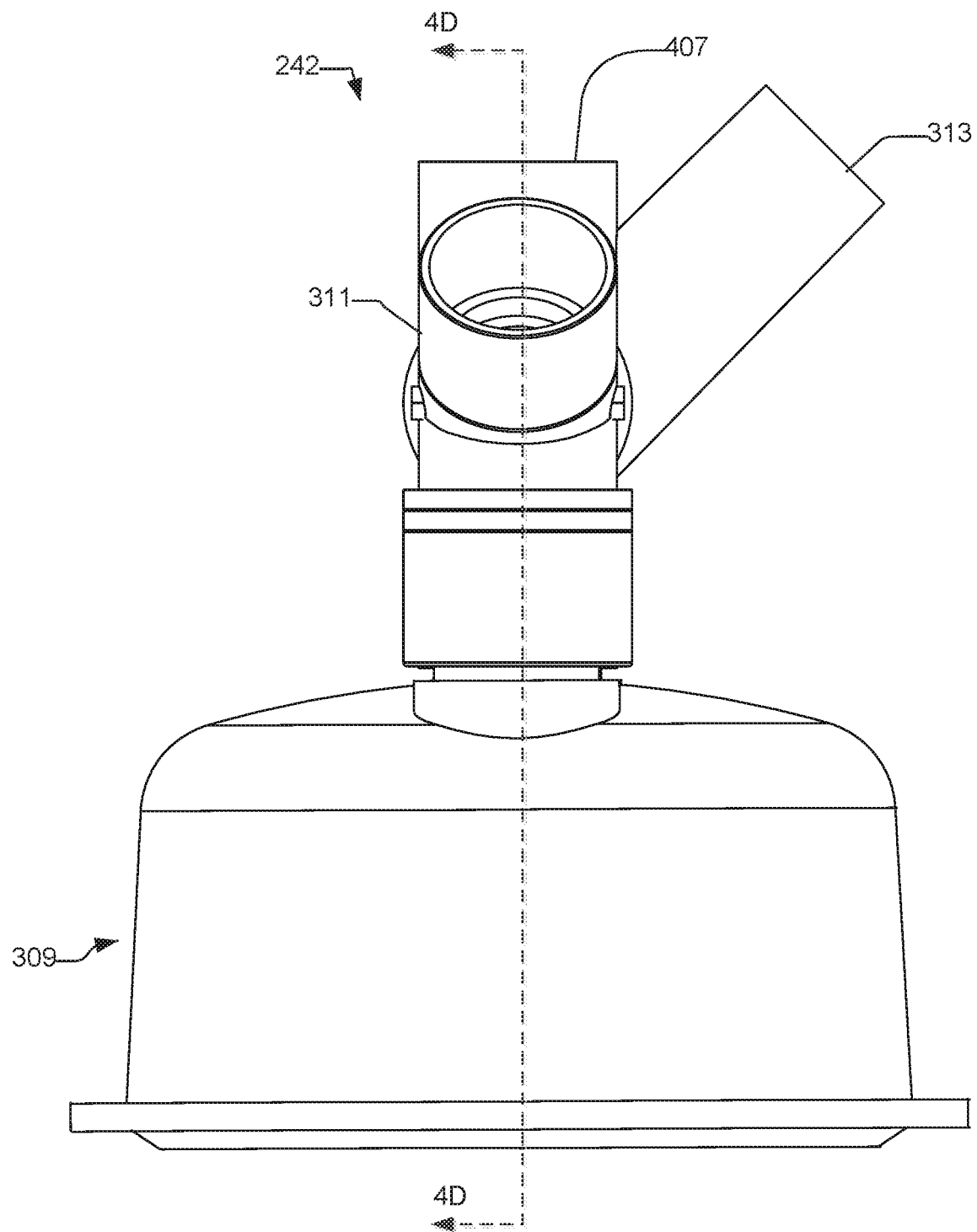
Figure 4D:
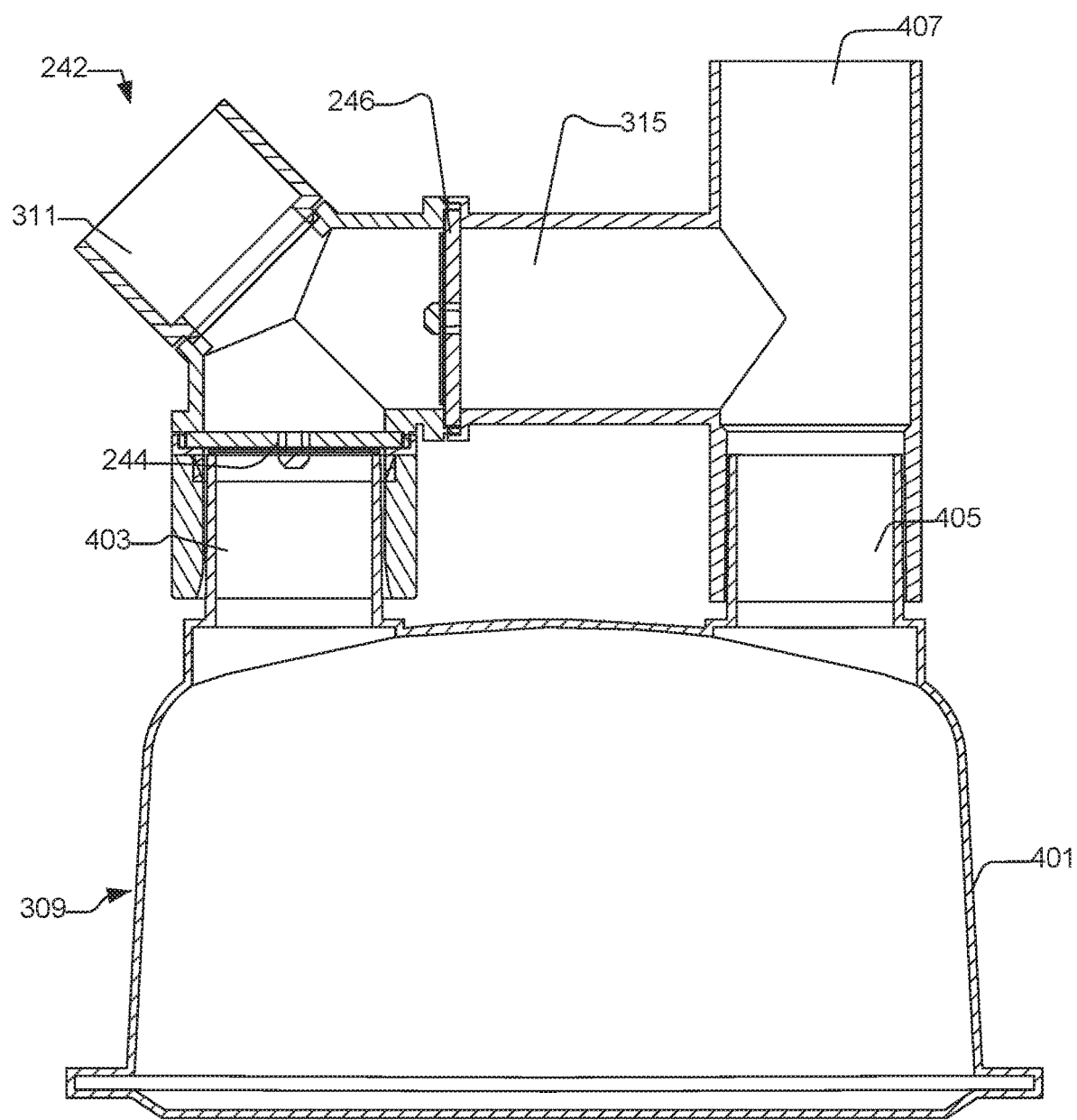

FIGS. 4A-4D illustrate various views of an embodiment of the bypass system 242 coupled to the chamber 309 of a humidifier. FIG. 4A is a perspective view, FIG. 4B is a partially exploded view, FIG. 4C is a side view, and FIG. 4D is a cross-section taken along line 4D-4D in FIG. 4C. Referring to FIGS. 4A-4D together, the bypass system 242 is engaged with the chamber 309, and the chamber 309 can be configured to be coupled to a standard commercially available humidifier base. Once coupled to the humidifier base, liquid within the chamber 309 can be heated. The chamber 309 in the embodiment shown in FIGS. 4A-4D includes a body 401 with a first stem 403 and a second stem 405 projecting away from the body 401. The first conduit 311 of the bypass system 242 engages the first stem 403 of the chamber 309, and the first valve 244 is within the first conduit 311 such that gas passing through the first conduit 311 and into the body 401 of the chamber 309 through the first stem 403 must pass through the first valve 244. As described above with respect to FIG. 3, the first conduit 311 of the bypass system 242 connects to the first tube 301 of the patient circuit 110, which delivers gases to and from the ventilator 100.

The second conduit 313 of the bypass system 242 couples to the second stem 405 of the chamber 309. As noted previously, the second conduit 313 of the bypass system 242 connects to the second tube 303 of the patient circuit 110, which connects to the patient connector and delivers gases to and from the patient. The bridge 315 extends between the first conduit 311 and the second conduit 313 of the bypass system 242 and the second valve 246 is in the bridge 315.

The bypass system 242 can also have a re-filling port 407 coupled to the second stem 405 of the chamber 309. The re-filling port 407 can share a portion of tubing with the second conduit 313 such that liquid can be provided to the chamber 309 through the re-filling port 407. In other embodiments, the chamber 309 can be filled through a separate port.

Figure 5A:
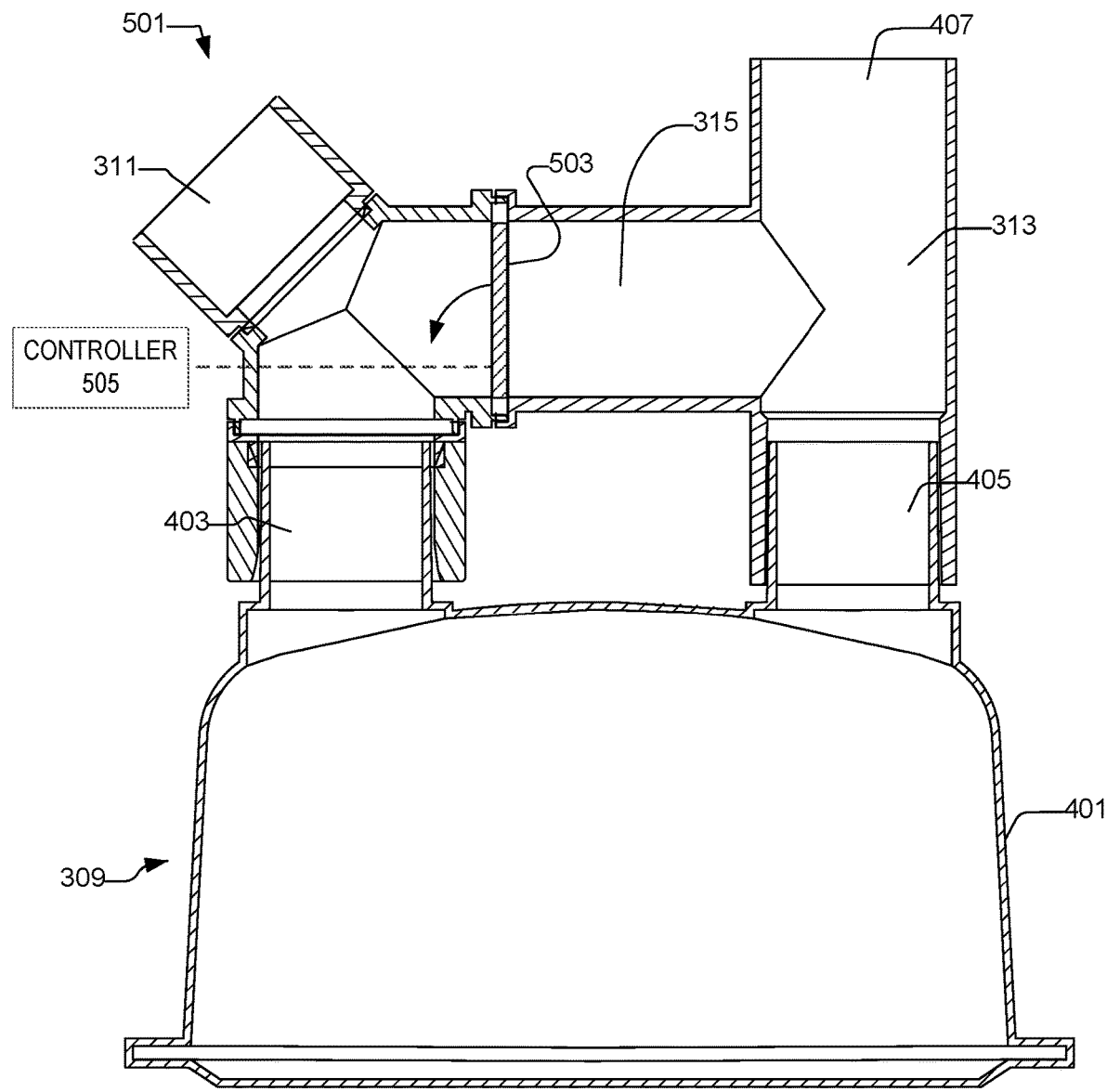
FIGS. 5A and 5B illustrate cross-sectional views of another embodiment of a humidifier bypass system.
Figure 5B:
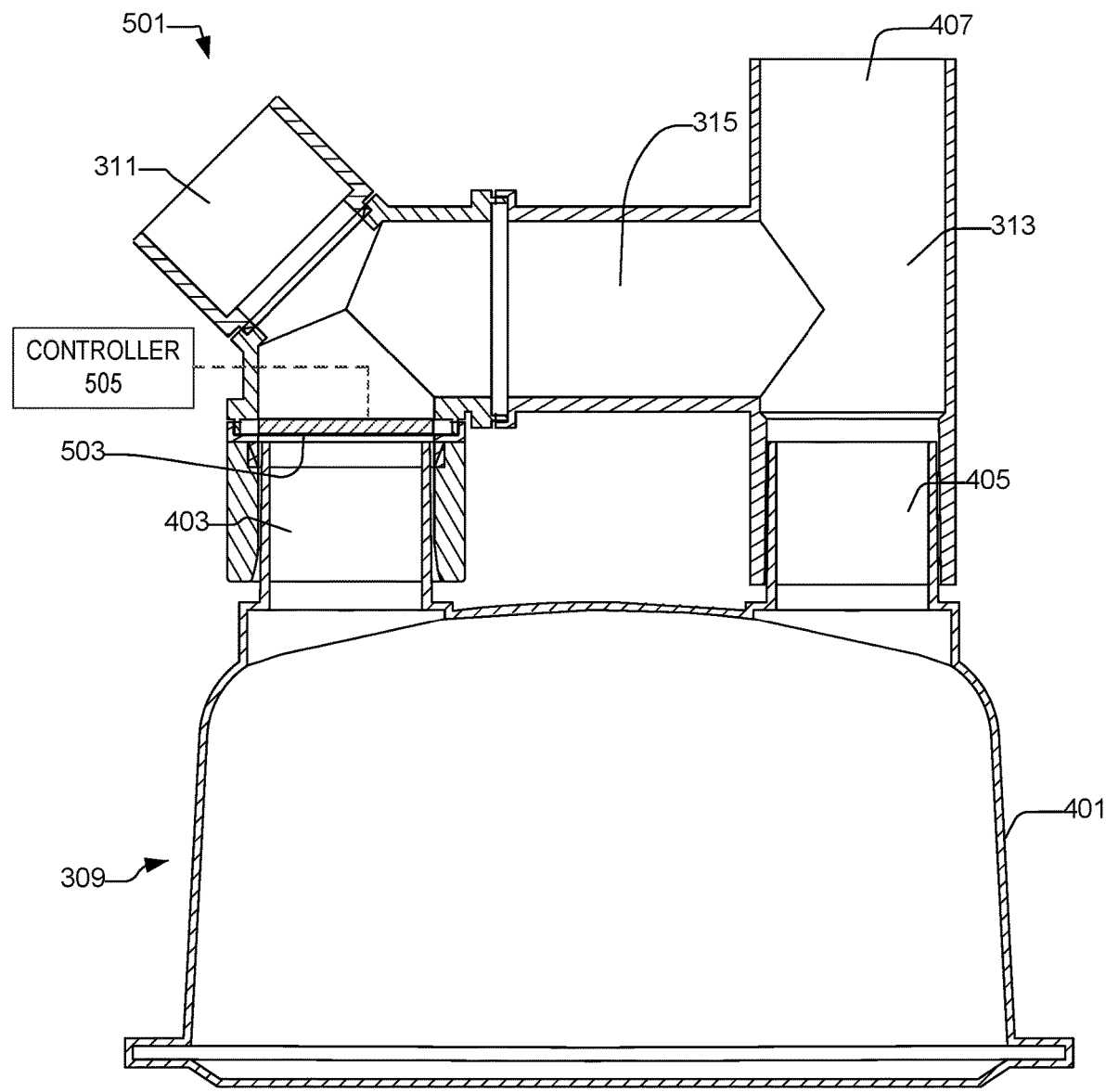

FIGS. 5A and 5B illustrate cross-sectional views of another embodiment of a humidifier bypass system 501 in accordance with the present technology. The bypass system 501 can be generally similar to the bypass system 242 system illustrated in FIGS. 4A-4D, except that the bypass system 501 includes a single controllable valve 503 coupled to a controller 505 integrated in the control system 174 described above with respect to FIG. 1. The valve 503 can be moved between a first position (FIG. 5A) and a second position (FIG. 5B) in response to signals received from the controller 505. In the first position (FIG. 5A), the valve 503 allows inspiration or insufflation gases to pass through the first conduit 311, through the first stem 403, and into the chamber 309 where the gases are humidified before exiting via the second stem 405 and the second conduit 313 to the patient. In the second position (FIG. 5B), the valve 503 allows exsufflating gases to pass through the second conduit 313 across the bridge 315 and out through the first conduit 311 without passing through the chamber 309. When the valve 503 is in the second position, liquid in the chamber 309 is blocked from flowing back to the ventilator. The single controllable valve 503 therefore provides similar functionality to the two-valve system described above with respect to FIGS. 3-4D.

The above detailed descriptions of embodiments of the technology are not intended to be exhaustive or to limit the technology to the precise forms disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or"

in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system comprising:
   a cough-assist device having a first phase configured to provide insufflating gas to a patient circuit and a second phase configured to draw exsufflating gas from the patient circuit;
   a humidifier between the cough-assist device and a distal end of the patient circuit, the humidifier comprising a chamber (i) configured to contain water and/or water vapor and (ii) fluidically coupled to the cough-assist device and the patient circuit; and
   a bypass configured to direct insufflating gas from the ventilator through to the patient circuit such that the insufflating gas is humidified in the chamber, wherein the bypass is further configured to route exsufflating gas from the patient circuit to the cough-assist device such that at least a portion of the exsufflating gas bypasses the chamber when the chamber is fluidically coupled to the cough-assist device and the patient circuit, wherein the bypass comprises a first conduit extending away from the chamber and fluidically coupling the cough-assist device to the chamber, a second conduit extending away from the chamber and fluidically coupling the chamber to the distal end of the patient circuit, a bridge connecting and extending between the first conduit and the second conduit, the bridge spaced apart from the chamber, a first valve disposed in the first conduit at a position between the chamber and the bridge, and a second valve disposed in the bridge at a position between the first conduit and the second conduit.

2. The system of claim 1 wherein the cough-assist device comprises a ventilator configured to provide breathing assistance in a first mode and cough assistance in a second mode.

3. The system of claim 1 wherein the first valve is configured
   to (a) open in the presence of insufflating gas so that insufflating gas from the cough-assist device passes through the chamber and (b) close in the presence of exsufflating gas to prevent exsufflating gas from exiting the chamber; and
   the second valve is configured to (a) open in the presence of exsufflating gas from the patient circuit so that at least the portion of the exsufflating gas passes to the ventilator without passing through the chamber and (b) to close in the presence of insufflating gas.

4. The system of claim 1 wherein the first valve is a one-way valve configured to open towards the chamber in the presence of insufflating gas, and wherein the second valve is a one-way valve configured to open towards the first conduit in the presence of exsufflating gas.

5. A humidifier assembly, comprising: a chamber configured to retain liquid therein; a heater configured to deliver heat to liquid within the chamber; a first conduit extending away from the chamber and configured to fluidically couple a cough-assist device to the chamber; a second conduit extending away from the chamber and configured to fluidically couple the chamber to a patient circuit; a bridge connecting and extending between the first conduit and the second conduit, the bridge spaced apart from the chamber; an insufflation flowpath configured to receive insufflating gas from a cough-assist device and direct the insufflating gas through the chamber and to a patient circuit; and an exsufflation flowpath configured to receive exsufflating gas from the patient circuit and direct at least a portion of the exsufflating gas to the cough-assist device without passing through the chamber when the humidifier assembly is fluidically coupled to the cough-assist device and the patient circuit, wherein the chamber is positioned between the first conduit and the second conduit, and wherein both the insufflating gas and the exsufflating gas are routed through at least a portion of the first conduit and at least a portion of the second conduit.

6. A system comprising:
   a cough-assist device having an insufflating module configured to provide an insufflating gas flow to a patient circuit and an exsufflating module configured to draw an exsufflating gas flow from the patient circuit;
   a humidifier fluidically coupled to the cough-assist device and the patient circuit, the humidifier having a chamber configured to contain water and/or water vapor; and
   a bypass having a first flow path between the cough-assist device and the chamber, a second flow path between the chamber and the patient circuit, a third flow path between the first and second flow paths, and a valve system, wherein the valve system is configured to—
   (a) block the third flow path during insufflation so that the insufflation gas flow passes through the chamber via the first and second flow paths, and
   (b) open the third flow path and block the first flow path during exsufflation such that at least a portion of the exsufflation gas flow passes through the third flow path and bypasses the chamber when the humidifier is fluidically coupled to the cough-assist device and the patient circuit.

7. The system of claim 6 wherein the valve system comprises:
   a first passive valve in the first flow path between the chamber and an intersection between the first flow path and the third flow path; and
   a second passive valve in the third flow path.

8. The system of claim 7 wherein the first passive valve comprises a first check valve configured to open towards the chamber during insufflation, and wherein the second passive valve comprises a second check valve configured to open towards the first flow path during exsufflation.

9. The system of claim 6 wherein the valve system comprises a valve disposed in the first flow path at an intersection between the first flow path and the third flow path, the valve configured to:
   (a) block the third flow path during insufflation so that the insufflation gas flow passes into the chamber via the first flow path, and (b) open the third flow path and block the first flow path during exsufflation such that at least the portion of the exsufflation gas flow passes through the third flow path and bypasses the chamber.

10. A humidifier assembly, comprising:
a chamber configured to retain liquid therein;
a heater configured to deliver heat to liquid within the chamber; and a bypass, wherein the bypass comprises:
a first conduit extending away from the chamber and configured to fluidically couple a cough-assist device to the chamber; a second conduit extending away from the chamber and configured to fluidically couple the chamber to a patient circuit; a bridge connecting and extending between the first conduit and the second conduit, the bridge spaced apart from the chamber; a first valve disposed in the first conduit at a position between the chamber and the bridge; a second valve disposed in the bridge at a position between the first conduit and the second conduit
an insufflation flowpath configured to receive insufflating gas from a cough-assist device and direct the insufflating gas through the chamber and to a patient circuit; and
an exsufflation flowpath configured to receive exsufflating gas from the patient circuit and direct at least a portion of the exsufflating gas to the cough-assist device without passing through the chamber when the humidifier assembly is fluidically coupled to the cough-assist device and the patient circuit.

11. The humidifier assembly of claim 10, wherein the insufflation flowpath passes through the first valve.

12. The humidifier assembly of claim 11 wherein the exsufflation flowpath does not pass through the first valve.

13. The humidifier assembly of claim 11, wherein the exsufflation flowpath passes through the second valve.

14. The humidifier assembly of claim 13 wherein the insufflation flowpath does not pass through the second valve.

15. A method for providing cough assistance to a patient, the method comprising:
delivering insufflating gas from a cough-assist device to a patient via a patient circuit, wherein the patient circuit has a first conduit and a second conduit; and
withdrawing exsufflating gas from the patient via the patient circuit, wherein at least a portion of the exsufflating gas bypasses a humidifier fluidically coupled to the cough-assist device and the patient circuit before reaching the cough-assist device, wherein the humidifier is positioned between the first conduit and second conduit, and wherein both the insufflating gas and exsufflating gas are routed through at least a portion of the first conduit and at least a portion of the second conduit.

16. The method of claim 15 wherein withdrawing exsufflating gas comprises providing a pressure between negative 30-70 cm $H_2O$ in the patient circuit.

17. The method of claim 15 wherein delivering insufflating gas comprises passing the insufflating gas through a chamber in the humidifier, thereby humidifying the insufflating gas before it reaches the patient.

18. The method of claim 15 wherein withdrawing the exsufflating gas comprises passing at least a portion of the exsufflating gas through a bypass coupled to the humidifier.

19. The method of claim 18 wherein the bypass comprises:
a first valve configured to (a) open while delivering the insufflating gas so that the insufflating gas from the cough-assist device passes through a chamber in the humidifier and (b) close in the presence of exsufflating gas to prevent exsufflating gas from exiting the chamber; and
a second valve configured to (a) open while withdrawing the exsufflating gas from the patient circuit so that at least the portion of the exsufflating gas passes to the ventilator without passing through the chamber and (b) to close in the presence of insufflating gas.

* * * * *